US007682618B2

(12) United States Patent
Bavari et al.

(10) Patent No.: US 7,682,618 B2
(45) Date of Patent: Mar. 23, 2010

(54) GENERATION OF VIRUS-LIKE PARTICLES AND USE AS PANFILOVIRUS VACCINE

(75) Inventors: Sina Bavari, Frederick, MD (US); M. Javad Aman, Gaithersburg, MD (US); Alan L. Schmaljohn, Millers, MD (US); Kelly L. Warfield, Adamstown, MD (US); Dana Swenson, Tucson, AZ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 76 days.

(21) Appl. No.: 11/105,031

(22) Filed: Apr. 13, 2005

(65) Prior Publication Data

US 2005/0266023 A1 Dec. 1, 2005

Related U.S. Application Data

(63) Continuation-in-part of application No. 10/289,839, filed on Nov. 7, 2002, now abandoned.

(60) Provisional application No. 60/338,936, filed on Nov. 7, 2001, provisional application No. 60/562,800, filed on Apr. 13, 2004, provisional application No. 60/562,801, filed on Apr. 13, 2004.

(51) Int. Cl.

| | |
|---|---|
| *A61K 39/12* | (2006.01) |
| *C12Q 1/70* | (2006.01) |
| *C12N 7/00* | (2006.01) |
| *C12N 5/10* | (2006.01) |

(52) U.S. Cl. ..................... 424/204.1; 435/5; 435/235.1; 435/325; 435/348

(58) Field of Classification Search ............. 424/199.1, 424/204.1, 186.1; 435/5
See application file for complete search history.

(56) References Cited

U.S. PATENT DOCUMENTS

| | | | | |
|---|---|---|---|---|
| 6,517,842 B1 * | 2/2003 | Hevey et al. | ............. | 424/199.1 |
| 7,211,378 B2 | 5/2007 | Kawaoka et al. | | |
| 2003/0099668 A1 * | 5/2003 | Bachmann et al. | ....... | 424/204.1 |
| 2005/0180993 A1 * | 8/2005 | Nabel et al. | .............. | 424/204.1 |

FOREIGN PATENT DOCUMENTS

| | | |
|---|---|---|
| WO | WO0000617 | 1/2000 |

OTHER PUBLICATIONS

Hart, "Vaccine research efforts for filoviruses," International Journal for Parasitology, 33, pp. 583-595 (2003).*

Warfield et al., "Filovirus-like particles as vaccines and discovery tools," Expert Rev. Vaccines, 4(3), pp. 429-440 (2005).*

Lundsgaard, "Filovirus-like particles detected in the leafhopper Psammotettix alienus," Virus Research 48, 35-40 (1997).*

Calain et al., "Ebola Virus Defective Interfering Particles and Persistent Infection," Virology 262, pp. 114-128 (1999).*

Jasenosky et al, "Ebola Virus VP40-Induced Particle Formation and Association with the Lipid Bilayer," Journal of Virology, vol. 75, No. 11, pp. 5205-5214 (2001).*

Bavari et al (Journal of Experimental Medicine 195:593-602, 2002).*

Wilson et al (Journal of Virology 75:2660-2664, 2001).*

Swenson et al. "Monovalent virus-like particle vaccine protects guinea pigs and nonhuman primates against infection with multiple Marburg viruses." Expert Rev. Vaccines 7(4): 417-429, 2008.*

Warfield et al. "Ebola Virus-Like Particle-Based Vaccine Protects Nonhuman Primates against Lethal Ebola Virus Challenge." Journal of Infectious Diseases 196 (Suppl. 2): S430-S437, 2007.*

Harty, R. N. et al., 2000. A PPxY motif within the VP40 protein of Ebola virus interacts physically and functionally with a ubiquitin ligase: Implications for filovirus budding. PNAS 97, 13871-13876.

* cited by examiner

*Primary Examiner*—Mary E Mosher
(74) *Attorney, Agent, or Firm*—Elizabeth Arwine

(57) ABSTRACT

In this application are described filovirus-like particles for both Ebola and Marburg and their use as a diagnostic and therapeutic agent as well as a filovirus vaccine. Also described is the association of Ebola and Marburg with lipid rafts during assembly and budding, and the requirement of functional rafts for entry of filoviruses into cells.

58 Claims, 22 Drawing Sheets

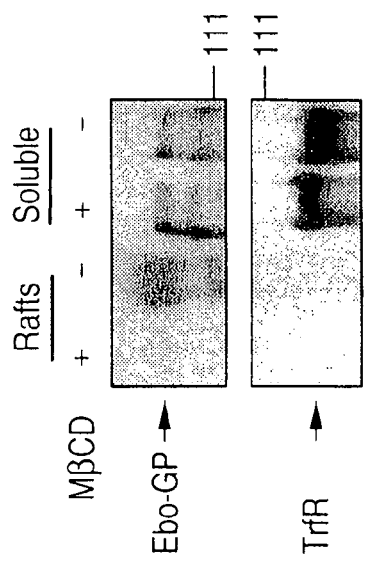
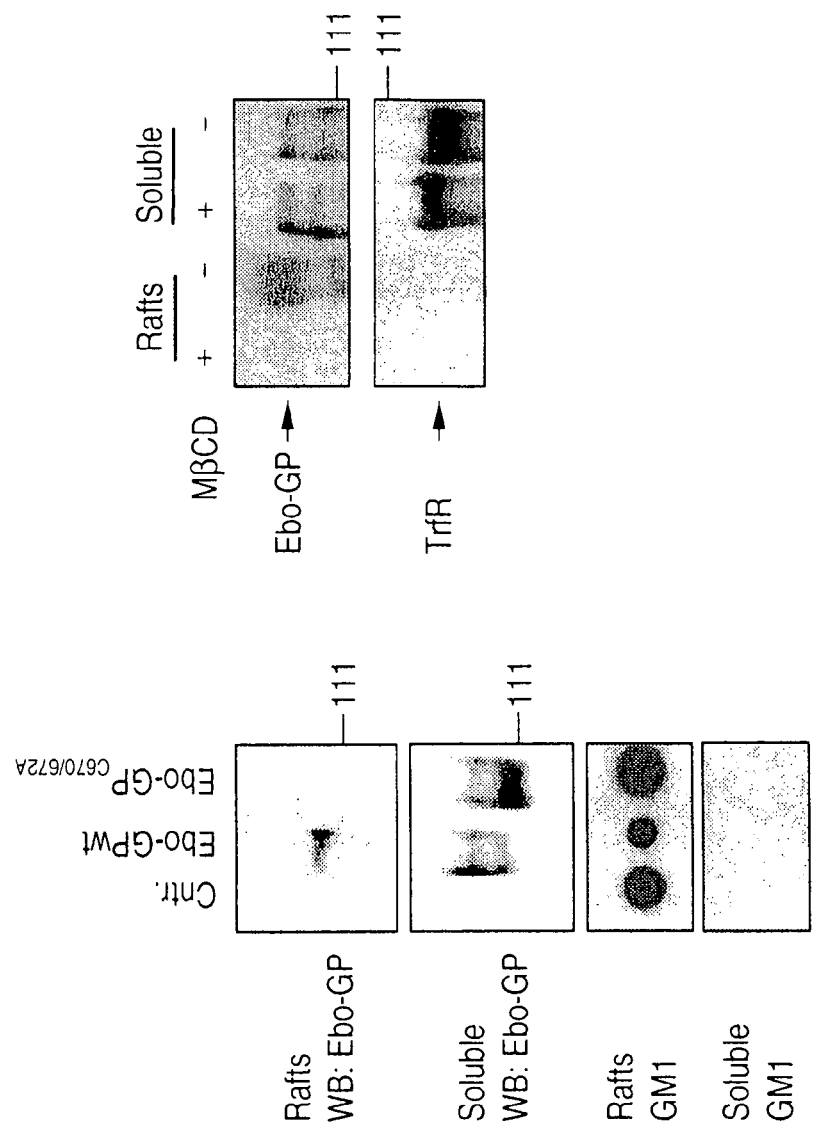
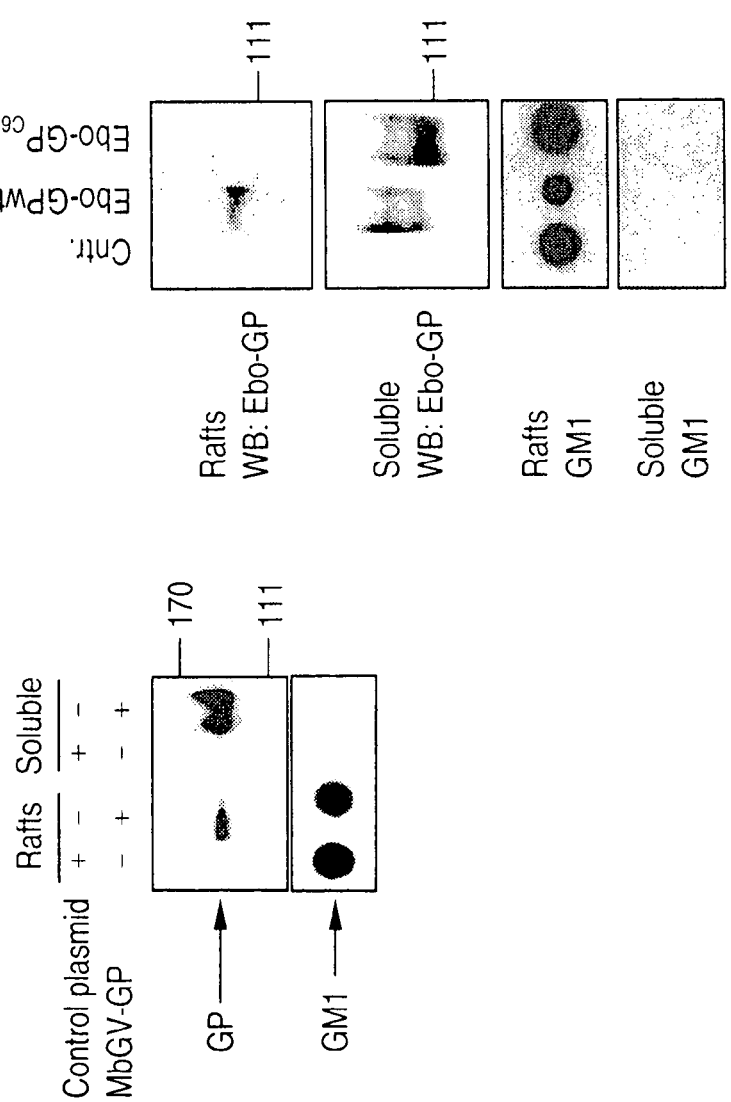

FIG. 3B

Infection: Ebola
Fraction: R S | R S
GP
VP40
HepG2 cells

FIG. 3A

Infection: MBGV | Inact. MBGV
Fraction: I S | I S
N.S 79
61
49
24
NP
VP35/40
1 2 3 4 5
Human Primary Monocytes

FIG. 3C

3D reconstruction

Single section

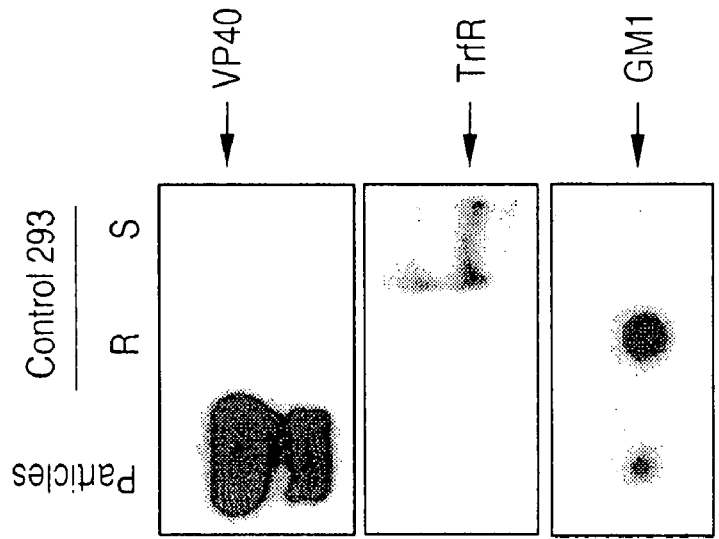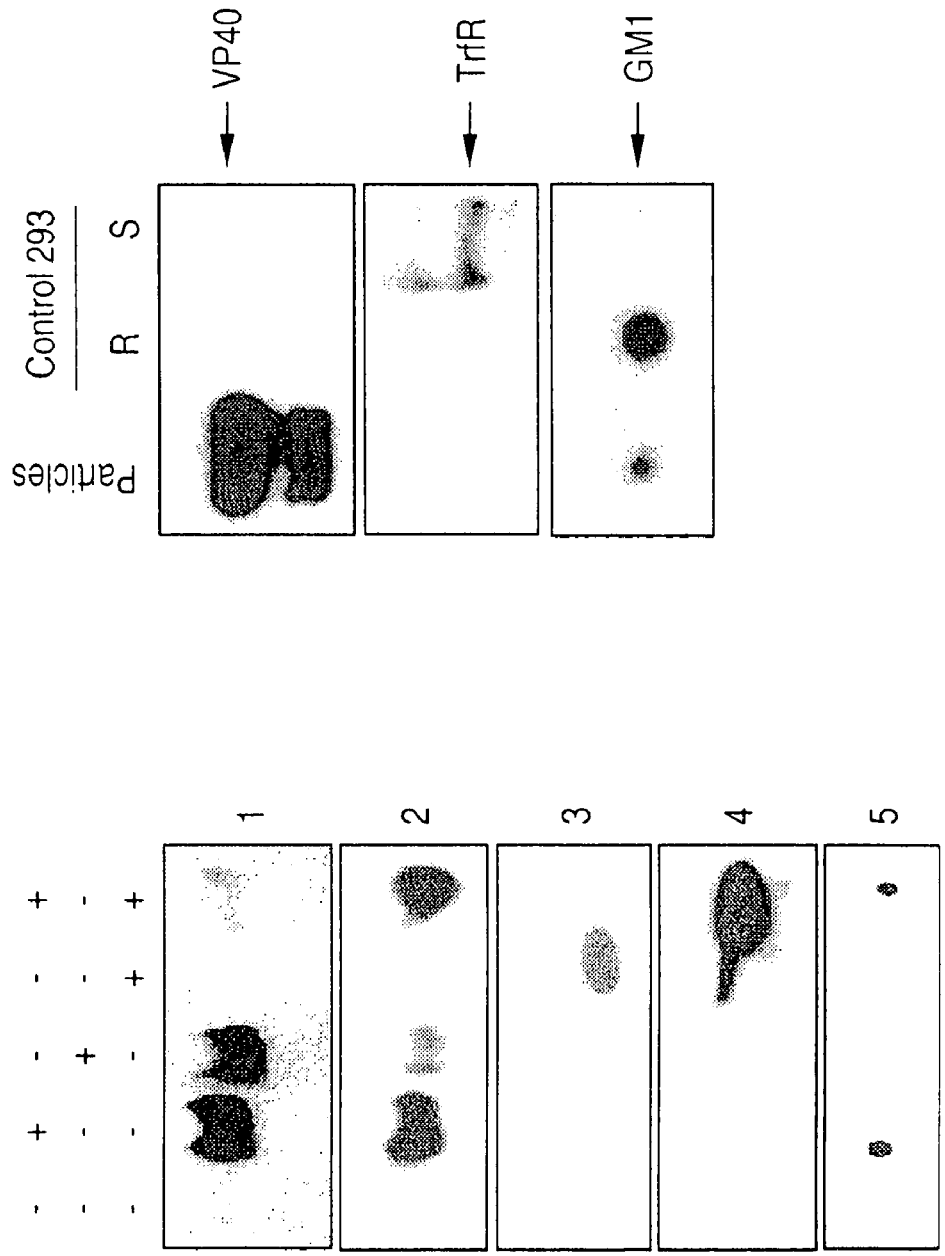

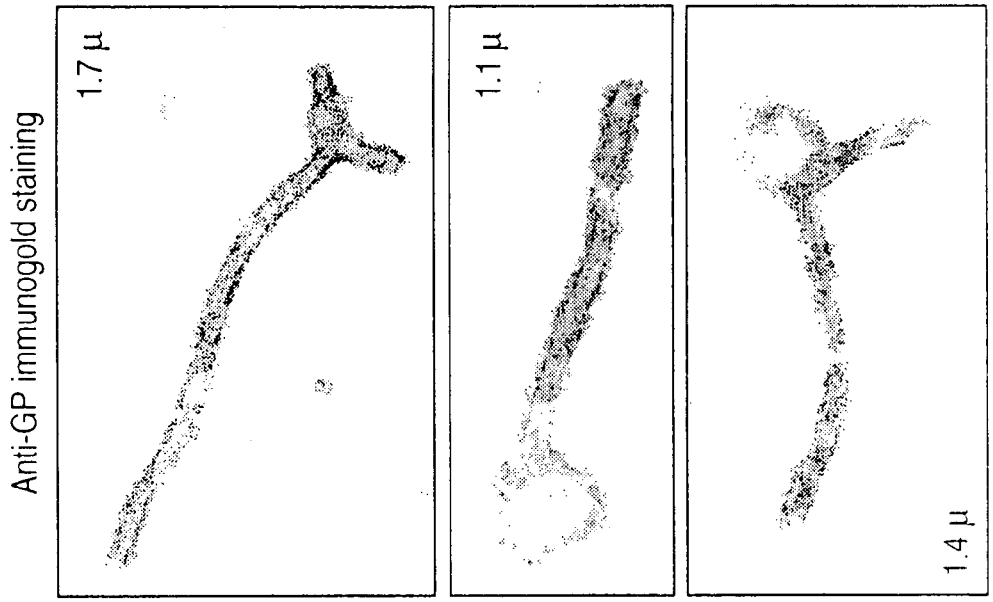
FIG. 6B Anti-GP immunogold staining
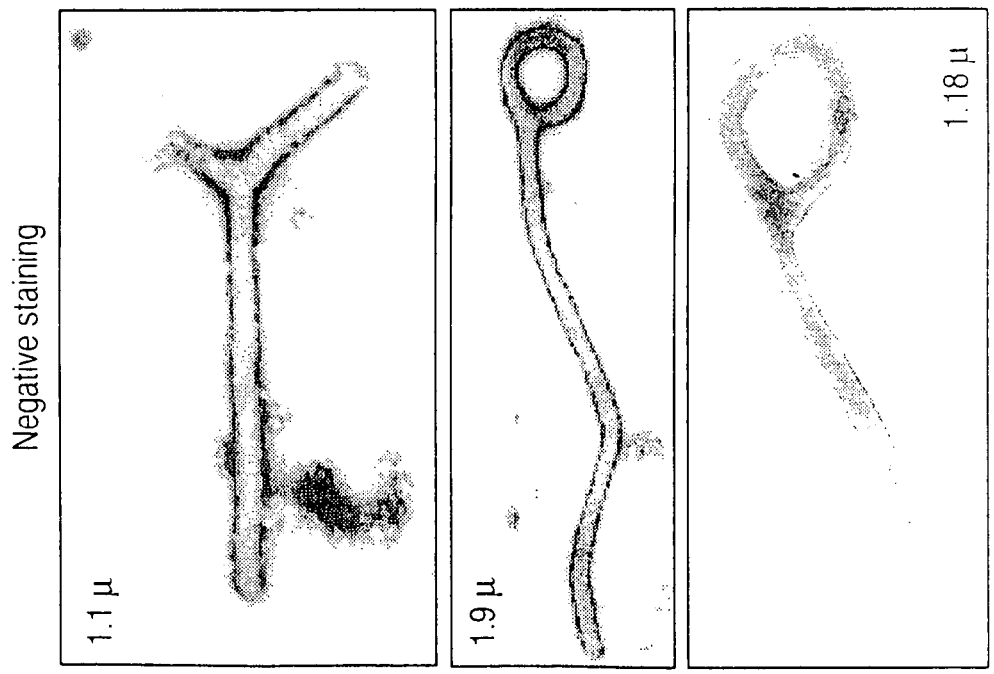
FIG. 6A Negative staining

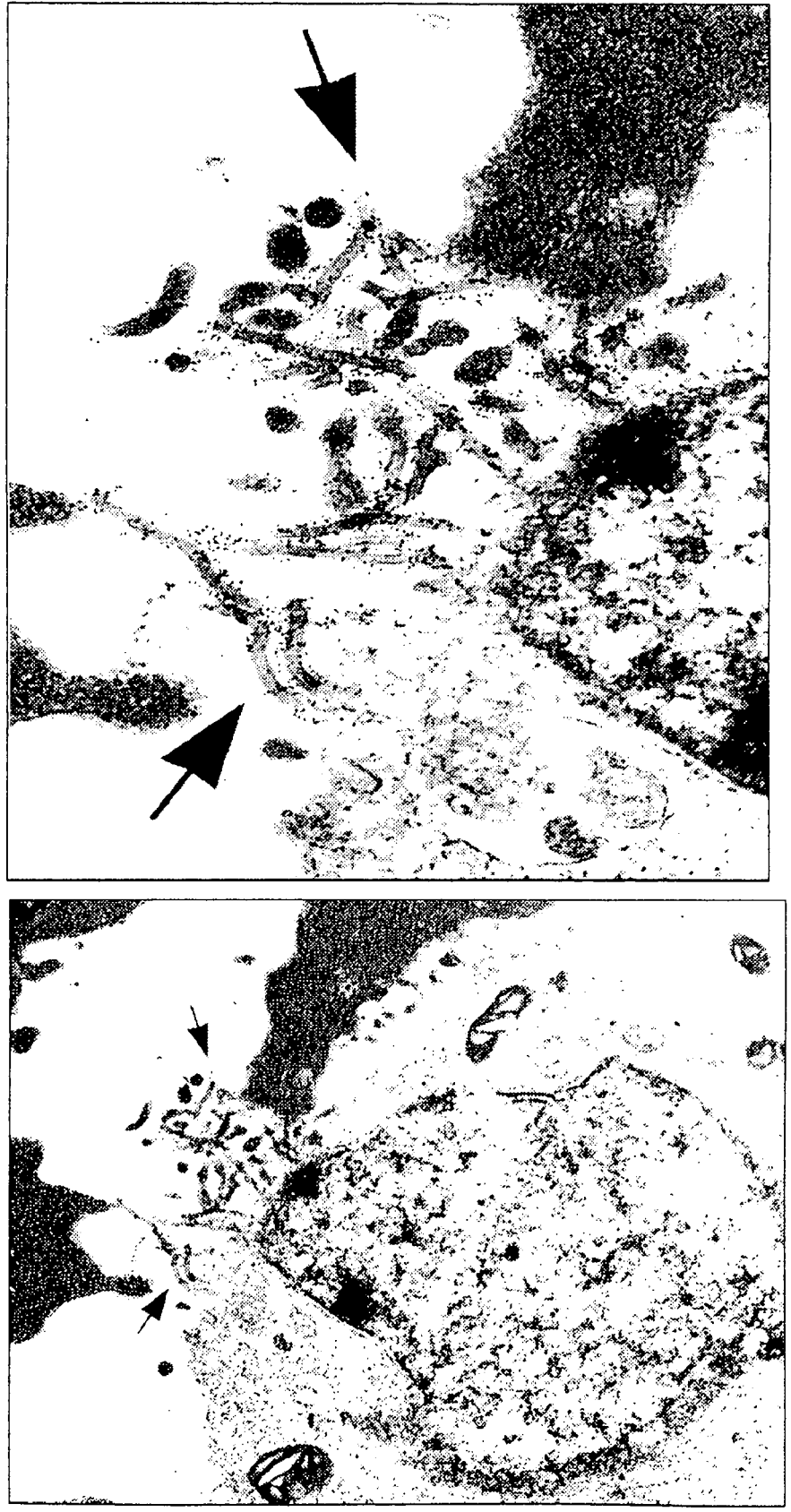

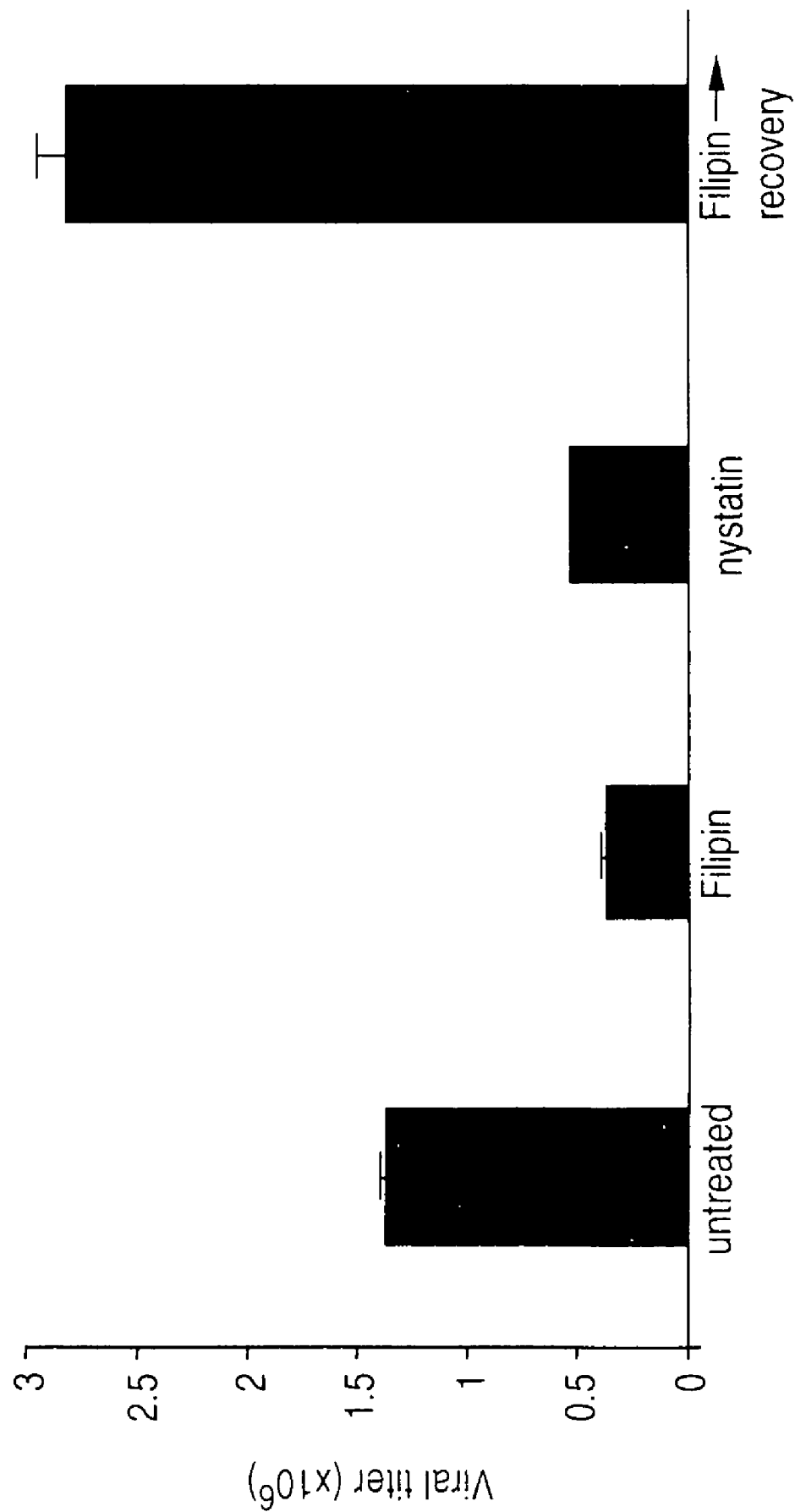

GENERATION OF VIRUS-LIKE PARTICLES AND USE AS PANFILOVIRUS VACCINE

This application is a continuation-in-part application of U.S. application Ser. No. 10/289,839 filed on Nov. 7, 2002 now abandoned, which claims the benefit of priority under 35 U.S.C. 119(e) from U.S. Application Ser. No. 60/338,936 filed on Nov. 7, 2001, now expired. This application also claims benefit of priority under 35 U.S.C. 119(e) from U.S. Application Ser. No. 60/562,800 and 60/562,801 filed on Apr. 13, 2004, all of which are herein incorporated by reference in their entirety.

INTRODUCTION

The filoviruses Ebola (EBOV) and Marburg (MBGV) are two of the most pathogenic viruses in humans and non-human primates (Feldman and Klenk, 1996, Adv. Virus Res. 47, 1), which cause a severe hemorrhagic fever (Johnson et al., 1997, Lancet 1, no. 8011, P. 569). The mortality rates associated with infections of Ebola or Marburg virus are up to 90% (Feldman and Klenk, 1996, supra; Johnson et al., 1997, supra). Although natural outbreaks have been geographically restricted so far, limited knowledge of the mechanisms of pathogenicity, potential of aerosol transmission (Jaax et al., 1995, Lancet 346, no. 8991-8992, 1669), unknown natural reservoir, and lack of immunological and pharmacological therapeutic measures, pose a challenge to classification of the public health threat of Marburg and Ebola viruses.

Currently, there are no vaccines or therapeutics available to prevent or treat filovirus infections. Classical, subunit, DNA, and vector-based vaccine strategies have been tested for protective efficacy against filovirus challenge in rodents and nonhuman primates (reviewed in Hevey et al., 1997, Virology 239, 206-16; Hevey et al., 2001, Vaccine 20, 586-93). Several vaccine candidates, including DNA, liposome-encapsulated inactivated virus, Venezuelan equine encephalitis virus replication-deficient particles (VRP) expressing filovirus proteins, have been used with varying degree of success in the mouse and guinea pig models of filovirus infection (Hevey et al, 1997, supra; Hevey et al., 1998, Virology 251, 28-37; Pushko et al., 2000, Vaccine 19, 142-153; Rao et al., 2002, J. Virol. 76, 9176-85; Vanderzanden et al., 1998, Virology 246, 134-144; Wilson et al., 2001, Virology 286, 384-90; Wilson and Hart, 2001, J. Virol. 75, 2660-4). For protection against MARV infection, a VRP vaccine encoding MARV GP was completely efficacious in both guinea pigs and nonhuman primates (Hevey et al, 1998, supra; Hevey et al., 2001, supra). Additionally, vaccinating guinea pigs or nonhuman primates with a DNA vaccine encoding GP or purified GP is only partially protective against MARV challenge (Hevey et al., 1997, supra; Hevey et al., 2001, supra; Riemenschneider et al., 2003, Vaccine 21, 4071-80). Administration of DNA vaccine encoding GP followed by >$10^{10}$ plaque-forming units (pfu) of a replication-defective, adenovirus-vectored vaccine expressing GP or the adenovirus vaccine alone expressing GP and nucleoprotein (NP) protects nonhuman primates against EBOV challenge (Nabel, G. J., 2003, Virus Res. 92, 213-17; Sullivan et al., 2003, Nature 424, 681-4; Sullivan et al., 2000, Nature 408, 605-9). Collectively, these efforts indicate that protection against lethal filovirus infection is attainable. Unfortunately, questions remain about many of the vaccine strategies used thus far, including acceptable vaccine doses, safety considerations, the impact of prior immunity to the vaccine vector, and the ability of these vaccine strategies to cross-protect against multiple strains of EBOV and MARV (Hart, M. K., 2003, Vaccine research efforts for filoviruses. International Journal for Parasitology 33, 583-595; Hevey et al., 2001, supra; Hevey et al., 2001, supra; Yang et al., 2003, J. Virol. 77, 799-803). Therefore, alternate approaches to filovirus vaccines are still needed.

Efforts to develop therapeutics against Ebola and Marburg have been hampered, in part, by poor understanding of the process of filovirus entry and budding at the molecular level. Understanding the nature of interactions between filoviruses and the host, both at the cellular and organism levels, is essential for successful development of efficacious prophylactic and therapeutic measures.

Both entry and release of enveloped virus particles are dependent on an intimate interaction with components of the cellular membranes. While the plasma membrane was initially envisioned as a fluid, randomly arranged lipid bilayer with incorporated proteins, recent advances demonstrate that this important cellular barrier is more sophisticated and dynamic than portrayed by the original simplistic models. Cholesterol-enriched regions in the lipid bilayer have been recently defined that adopt a physical state referred to as liquid-ordered phase displaying reduced fluidity and the ability for lateral and rotational mobility (Simons and Ikonen, 1997, Nature 387, 569; Brown and London 1998, Annu. Rev. Cell Dev. Biol. 14, 111). These low density, detergent-insoluble microdomains, known as lipid rafts, accommodate a selective set of molecules such as gangliosides, glycosphingolipids, glycosylphosphatidylinositol (GPI) anchored proteins, and signaling proteins such as Src family kinases, T and B cell receptors, and phospholipase C (Simons and Ikonen, 1997, supra; Brown and London 2000, J. Biol. Chem 275, 17221; Simons and Toomre, 2000, Nature Rev. 1, 31; Aman and Ravichandran, 2000, Cur. Biol. 10, 393, Xavier et al., 1998, Immunity 8, 723). By virtue of these unique biochemical and physical properties, lipid rafts function as specialized membrane compartments for channeling certain external stimuli into specific downstream pathways (Cheng et al., 2001, Semin. Immunol. 13, 107; Janes et al., 2000, Semin. Immunol. 12, 23), act as platforms in cell-cell interactions (Viola et al., 1999, Science 283, 680; Moran and Miceli, 1998, Immunity 9, 787), and have also been implicated in membrane trafficking (Brown and London, 1998, supra; Verkade and Simons, 1997, Histochem. Cell Biol. 108, 211). Lipid rafts are believed to perform such diverse functions by providing a specialized microenvironment in which the relevant molecules for the initiation of the specific biological processes are partitioned and concentrated (Brown and London, 2000, supra). Such compartmentalization may help the signals achieve the required threshold at the physiological concentrations of the stimuli. Partitioning in lipid rafts can also be perceived as a measure to perform functions in a more specific and efficient manner while keeping distinct pathways spatially separated.

Several lines of evidence suggest a role for cholesterol-enriched lipid rafts in host-pathogen interactions. Cholesterol has been shown to play a critical role for the entry of mycobacterium into macrophages (Gatfield and pieters, 2000, Science 288, 1647). Multiple components of influenza virus (Scheiffele et al., 1999, J. Biol. chem. 274, 2038), measles virus (Manie et al., 2000, J. Virol. 74, 305), and human immunodeficiency virus (HIV) (Nguyen and Hildreth, 2000, J. Virol. 74, 3264; Rousso et al., 2000, Proc. Natl. Acad. Sci. U.S.A. 97, 13523) have been shown to localize to lipid rafts. These lipid platforms have also been implicated in the budding of HIV and influenza virus (Scheiffele et al, 1999, supra; Nguyen and Hildreth, 2000, supra). Therefore, rafts, as tightly regulated specialized domains, may represent a coordination site for the intimate interactions of viral proteins required for the assembly and budding process. While involvement of rafts in virus entry has been postulated (Dimitrov, D. S. 2000, Cell 101, 687), supporting data on this issue have been reported only for HIV infection of certain T cell lines (Manes et al., 2000, EMBO Rep. 1, 190).

Therefore, there exists a need in the art for elucidation of the factors that affect filovirus assembly and disassembly. There is also a need for an efficient in vitro method for generation of genome-free virus-like particles which are stable, and retain immunogenic properties, i.e., those which present conformational, and more particularly, neutralizing epitopes expressed on the surface of native, intact filovirus.

Further, there is a need for elucidating the method by which filoviruses enter and exit cells. Once the method is known, treatments and agents for disrupting attachment, fusion or entry of the virus, i.e. infection, can be ascertained.

SUMMARY OF THE INVENTION

The present invention satisfies the needs discussed above. Using a variety of biochemical and microscopic approaches, we demonstrate the compartmentalization of Ebola and Marburg viral proteins in lipid rafts during viral assembly and budding. Our findings also show that filovirus trafficking, i.e. the entry and exit of filoviruses into and out of cells, is dependent on functional rafts. This study, thus, provides a deeper understanding of the molecular mechanisms of filovirus pathogenicity at the cellular level, and suggests raft integrity and/or raft components as potential targets for therapeutic interventions. We also report, for the first time, the raft-dependent formation of Ebola-based and Marburg-based, genome-free, virus-like particles (VLPs), which resemble live virus in electron micrographs. Such VLPs, besides being a research tool, are useful as vaccines against filovirus infections, and as vehicles for the delivery to cells of a variety of antigens artificially targeted to the rafts.

Therefore, the present invention relates to filovirus virus-like particles (VLPs) and a method for generating genome-free Ebola or Marburg VLPs in a mammalian transfection system. This method generates VLPs that resemble native virus. The virus-like particles are useful for transferring into a cell a desired antigen or nucleic acid which would be contained in the internal space provided by the virus-like particles.

It is one object of the present invention to provide a method for generating genome-free filovirus virus-like particles (VLPs), specifically, Ebola and Marburg VLPs. The method includes expression of virus GP and VP40 in cells. The VLP of the present invention are more native in the filovirus-like morphology and more native in terms of the conformation of virus spikes.

It is another object of the present invention to provide VLP-containing compositions. The compositions contain Ebola VLPs or Marburg VLPs or a combination of Ebola and Marburg VLPs for use as a vaccine, a delivery vehicle and in a diagnostic assay.

It is yet another object of the invention to provide a vaccine for inducing an immune response to a filovirus, namely Ebola or Marburg, said vaccine comprising Ebola VLP or Marburg VLP, respectively, or a combination of Ebola and Marburg VLPs.

It is another object of the invention to provide a method for encapsulating desired agents into filovirus VLP, e.g., therapeutic or diagnostic agents.

It is another object of the invention to provide filovirus VLPs, preferably Ebola VLPs or Marburg VLPs, which contain desired therapeutic or diagnostic agents contained therein, e.g. anti-cancer agents or antiviral agents.

It is still another object of the invention to provide a novel method for delivering a desired moiety, e.g. a nucleic acid to desired cells wherein the delivery vehicle for such moiety, comprises filovirus VLP.

It is another object of the invention to provide a diagnostic assay for the detection of Ebola or Marburg virus infection in a sample from a subject suspected of having such an infection. The method comprises detecting the presence or absence of a complex formed between anti-Ebola antibodies or anti-Marburg antibodies in the sample and Ebola VLPs or Marburg VLPs, respectively.

It is yet another object of the present invention to use noninfectious filovirus VLP in an in vitro assay for testing the efficacy of potential agents to inhibit or reduce filovirus entry into cells or budding from cells, i.e. infectivity.

It is another object of the invention to provide a method for identifying critical structural elements within filovirus proteins required for viral assembly and/or release. The method consists of detecting a change in VLP formation, assembly, or budding from a cell expressing filovirus mutant proteins as compared to a cell expressing wild type alleles of such mutations.

It is further an object of the invention to provide an immunological composition for the protection of mammals against Ebola or Marburg virus infection comprising Ebola or Marburg virus-like particles.

It is another object of the present invention to provide a method for evaluating effectiveness of an agent or chemical to block entry of filovirus into a cell, said agent or chemical able to alter the cell's lipid rafts, said method comprising introducing said agent or chemical to a cell and monitoring the effect of said agent or chemical by monitoring VLP entry or exit from a cell. Agents include chemicals, cellular agents or factors, and other viral agents.

BRIEF DESCRIPTION OF THE DRAWINGS

These and other features, aspects, and advantages of the present invention will become better understood with reference to the following description and appended claims, and accompanying drawings where:

FIGS. 1A, 1B, and 1C. Localization of filovirus glycoproteins in lipid rafts. 293T cells were transfected with Marburg GP (A), Ebo-GPwt, or Ebo-GP$_{C670/672A}$ (B), or a control plasmid, rafts were prepared by ultracentrifugation and GP was detected by immunoblotting. GM1 was detected by blotting with HRP-CTB in the corresponding fractions spotted on a nitrocellulose membrane, as a control for the quality of raft preparation. (C) 48 h after transfection of 293T cells with Ebola GP, a portion of cells were treated for 20 minutes with 10 mM methyl-b-cyclodextrin (MbCD) and another portion was left untreated. Raft and soluble fractions were prepared and analyzed by immunoblotting for GP (upper panel) and for the raft-excluded protein transferrin receptor (TrfR, lower panel).

FIGS. 3A, 3B and 3C. Localization of filovirus proteins in lipid rafts in infected cells. A. Primary human monocytes were infected with MBGV. After 24 h cells were lysed in 0.5% triton-X100 and detergent-soluble (S) and -insoluble (I) fractions were separated by centrifugation, samples were irradiated ($2 \times 10^6$ R), and analyzed by immunoblotting with a guinea pig anti-MBGV antibody to detect viral proteins NP and VP35/VP40 (lanes 3,4); lanes 1,2: uninfected control; lane 5: inactivated MBGV (1 mg). N.S.: non-specific band. B. HepG2 hepatocytes were infected with EBOV-Zaire, lysed, irradiated ($6 \times 10^6$ R), and rafts (R) and soluble (S) fractions were prepared by ultracentrifugation 24 hours post infection. Ebola GP and VP40 were detected by immunoblotting. C. Ebola-infected Vero E6 cells were irradiated ($4 \times 10^6$ R), fixed and stained for Ebola virus (red) and GM1 (green) at 4° C. and imaged by confocal microscopy; left panel: single section; right panel: 3D reconstruction of the compiled data.

FIGS. 5A and 5B. Release of Ebola GP and VP40 as GM1-containing particles. (A) 293T cells were transfected with the indicated plasmids, supernatants were cleared from floating cells by centrifugation and particulate material were pelleted through 30% sucrose by ultracentrifugation. The individual proteins were detected in the cell lysates and in the particulate material from supernatant by immunoblotting (IB). A fraction of cleared supernatant was subjected to immunoprecipitation using anti-GP mAb and analyzed for the presence of GM1 (lower panel) as described in the legend to FIG. 1. (B) The particulate material from cells transfected with GP+VP40 were further purified on a sucrose step gradient and the low density fraction was analyzed for the presence of VP 40 (top panel), TrfR (middle panel), and GM1 (lower panel). Rafts and soluble fractions from untransfected 293T cells were used as control.

FIGS. 6A, 6B, and 6C. Electron microscopic analysis of virus like particles generated by EBOV GP and VP40. Particles obtained by ultracentrifugation of the supernatants of 293T cells transfected with Ebola GP+VP40 were negatively stained with uranyl-acetate to reveal the ultrastructure (A), or stained with anti-Ebo-GP mAb followed by Immunogold rabbit anti mouse Ab (B), and analyzed by electron microscopy. The length of each particle is indicated in mm. (C) 293T cells transfected with Ebola GP+VP40 were immunogold-stained for Ebola GP, fixed, cut, and analyzed by electron microscopy. The picture depicts a typical site of VLP release from the cells, indicated by arrows. A magnification of the site of VLP release is also shown to better visualize the gold staining on the particles.

FIG. 7. Inhibition of Ebola infection by raft-disrupting agents filipin and nystatin. Vero E6 cells were left untreated or treated for 30 minutes with 0.2 mg/ml of filipin or 100 U/ml of nystatin at 37° C., washed extensively with PBS and infected with Ebola at an MOI of 1. As a control for lack of general toxicity and persistent effect on viral replication, upon treatment with filipin, cells were washed and incubated in medium for 4 h before infection with EBOV (Filipin (recovered). After 48 h supernatants were harvested and viral titers determined by plaque assay.

Figures 8A, 8B:
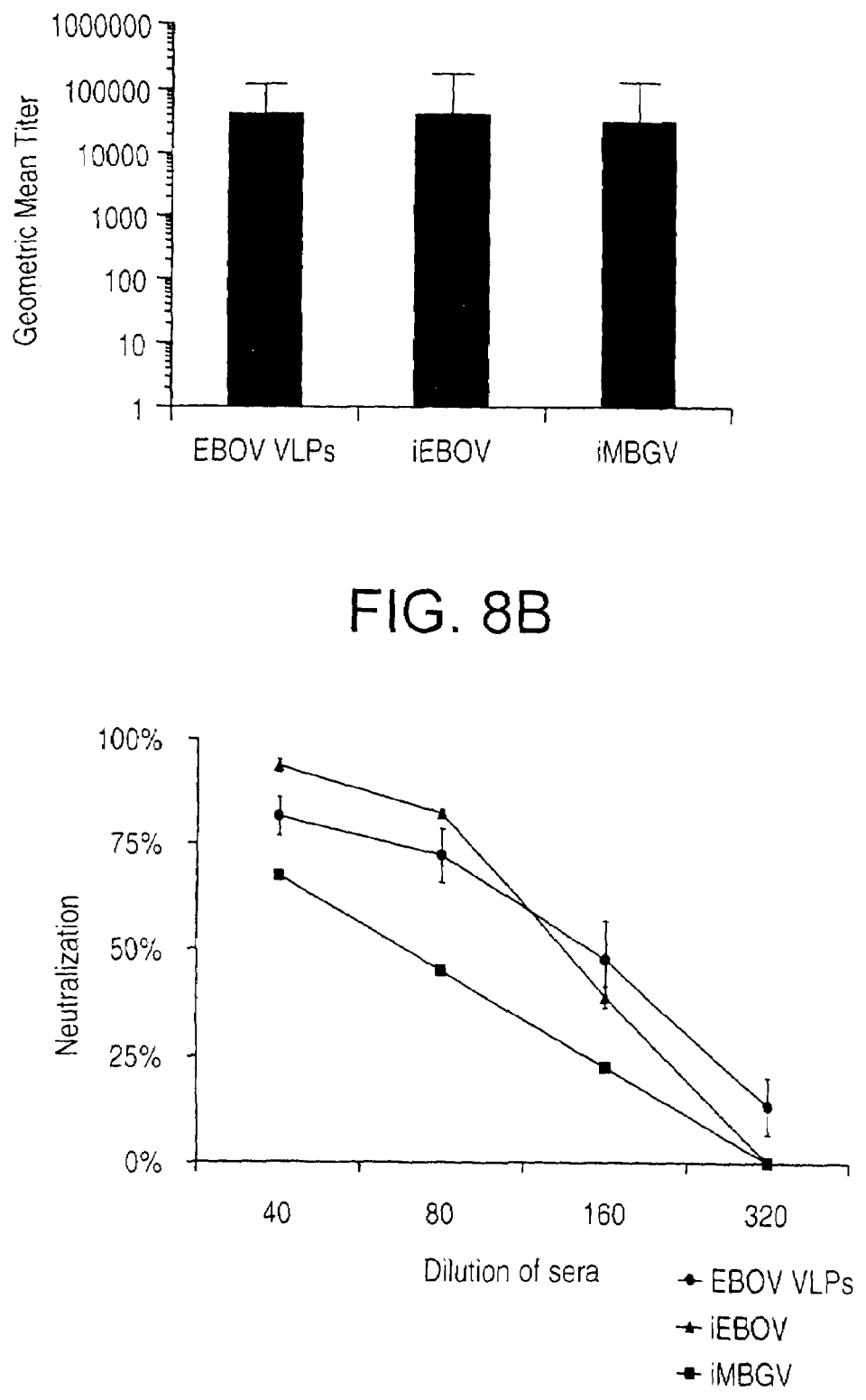

FIGS. 8A and 8B. Serum antibody responses in mice following intraperitoneal immunization with 40 ug of EBOV VLPs, inactivated Ebola (iEBOV) or Marburg (iMBGV) virus on days 0, 21, and 42. (A) Total IgG serum anti-Ebola antibodies were measured by ELISA 42 and 63 days post immunization (dpi) following the 2nd or 3rd vaccination, respectively. Ebola antibody titers were measured for individual mice and the results are graphed as the endpoint titer for each mouse. The number of mice with the same endpoint titer are noted on the graph. Closed and filled symbols represent the titer after second and third vaccination respectively. (B) Percent neutralization of Ebola virus infection in VeroE6 cells by sera of immunized mice. Two-fold dilutions of sera were tested for their ability to neutralize Ebola virus infection and are plotted as the mean of the percent neutralization for each group of immune sera as compared to mock-treated VeroE6 cells.

Figure 9:
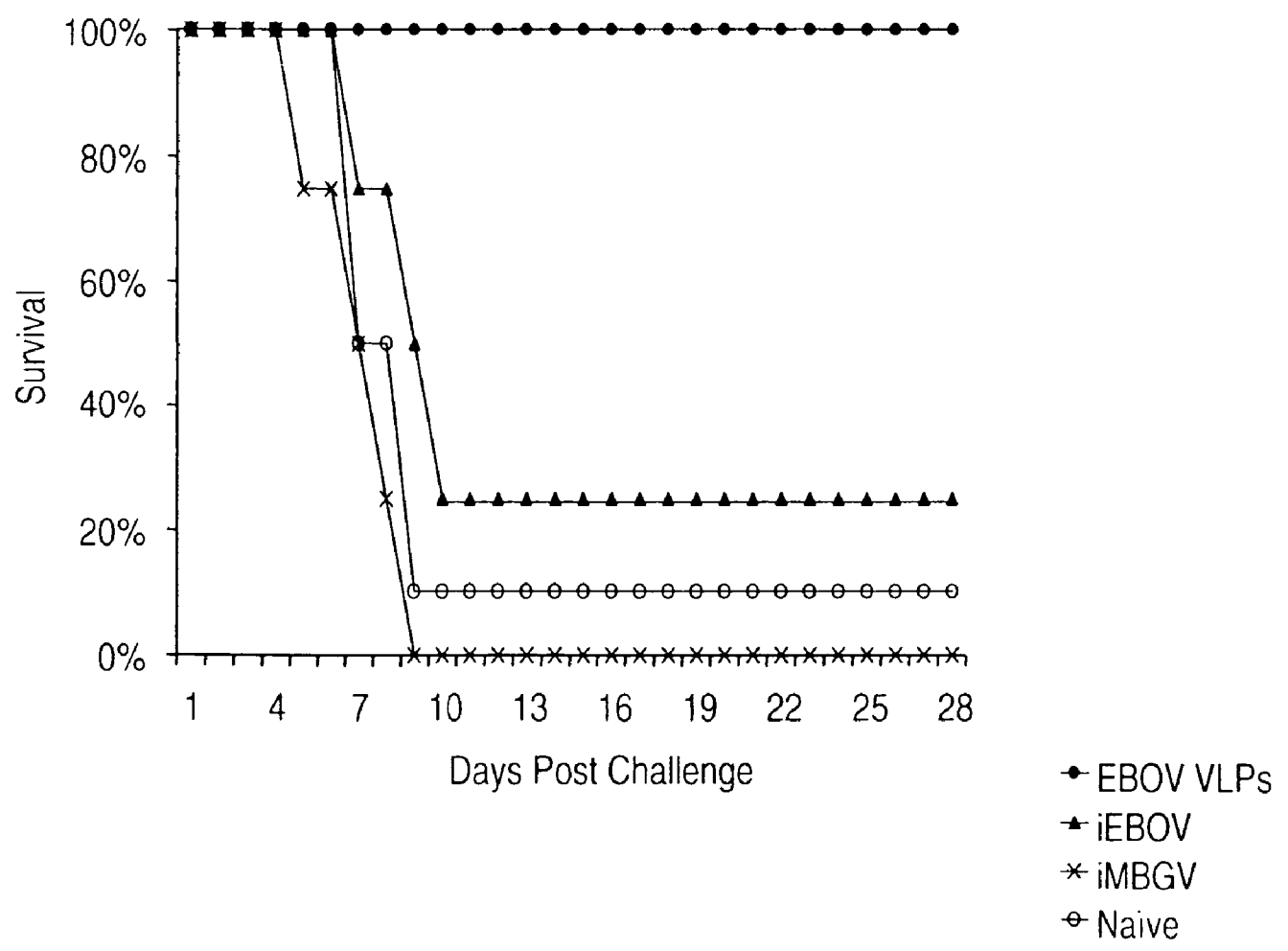

FIG. 9. Ebola (e)VLPs protect mice against challenge with mouse-adapted EBOV. Mice were immunized intraperitoneally with 40 ug of eVLPs, iEBOV or iMBGV on 0, 21, and 42 dpi. All mice were challenged on day 63 with 300 pfu of mouse-adapted Ebola virus. Results are plotted as percent survival for each immunization group.

FIGS. 11A and 11B. Humoral responses to VLP vaccination. Strain 13 guinea pigs were vaccinated with iMARV (n=5), mVLPs (n=5), eVLPs (n=5) in RIBI adjuvant, or adjuvant only (n=6) three times at three-week intervals. a-b, Serum samples from the guinea pigs were obtained three weeks after the first (1), second (2), or third (3) vaccination and four weeks after challenge (PC). Total-serum (a) anti-MARV or (b) Ebola virus (EBOV) antibodies were measured by ELISA. Antibody titers were measured in serum from individual guinea pigs and the results are graphed as the individual endpoint titers for each guinea pig in each group.

FIG. 12. Vaccination with mVLPs induces neutralizing antibody responses against MARV. Percent neutralization of MARV infection in Vero E6 cells by serum from guinea pigs vaccinated with inactivated MARV (iMARV) (filled circle, n=5), mVLP (filled triangle, n=5), or Ebola virus-like particles (eVLP, n=5) (open square) in RIBI adjuvant or adjuvant alone (star, n=6). Three-fold dilutions of serum were tested for their ability to neutralize MARV virus infection of VeroE6 cells and are plotted as the mean of the percent neutralization for each group of immune sera as compared to mock-treated Vero E6 cells. Error bars indicate the standard deviation of each group (n=5).

FIG. 21. Serum antibody responses and protection following vaccination of T cell knockout mice with Ebola VLPs. A. Wild-type C57B1/6 or /δT cell receptor (TCR), CD4+ or CD8+ T cell deficient mice were vaccinated with 10 μg each of eVLPs and QS-21 or QS-21 alone twice at 21-day intervals. Total serum anti-Ebola virus antibodies were measured 6 weeks after the last vaccination. The results are depicted as the endpoint titers of each mouse (circles). The data are representative of two experiments of similar design and outcome. B. eVLP-vaccinated T cell deficient or wild-type mice were challenged with 1000 pfu of mouse-adapted EBOV 6 weeks after the last vaccination. Results are plotted as percent survival for each vaccination group (n=10 per group).

DETAILED DESCRIPTION

Figure 2B:
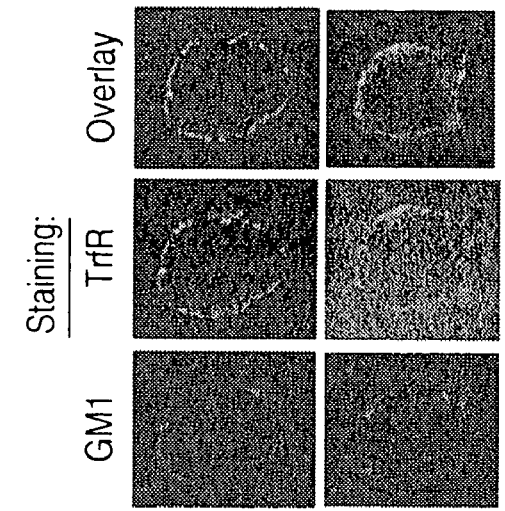
FIGS. 2A and 2B. Colocalization of filovirus glycoproteins with CM1 on intact cells. (A) 293T cells were transfected with the indicated GP, and stained at 4° C. with Alexa488-CTB (green) and anti-GP mAb followed by Alexa-647 conjugated anti-mouse antibodies (red), cells were fixed and imaged using confocal microscopy. Colocalization is represented by yellow appearance in the overlay (right panels). A 3-D reconstruction of the compiled data from 25 sections of a Ebo-GP transfected cell is also shown. (B) 293T cells were concurrently stained at 4° C. with Alexa-488 conjugated anti- TrfR antibody (green) and Rohdamin-CTB (red), fixed and analyzed by confocal microscopy. No colocalization between these two molecules was observed, evident by the lack of yellow appearance.

In the description that follows, a number of terms used in recombinant DNA, virology and immunology are extensively utilized. In order to provide a clearer and consistent understanding of the specification and claims, including the scope to be given such terms, the following definitions are provided.

Filoviruses. The filoviruses [e.g. Ebola virus (EBOV) and Marburg virus (MBGV)] cause acute hemorrhagic fever characterized by high mortality. Humans can contract filoviruses by infection in endemic regions, by contact with imported primates, and by performing scientific research with the virus. However, there currently are no available vaccines or effective therapeutic treatments for filovirus infection. The virions of filoviruses contain seven proteins which include a surface glycoprotein (GP), a nucleoprotein (NP), an RNA-dependent RNA polymerase (L), and four virion structural proteins (VP24, VP30, VP35, and VP40).

Subject. Includes human, animal, avian, e.g., horse, donkey, pig, mouse, hamster, monkey, chicken, and insect such as mosquito.

Virus-like particles (VLP). This refers to a structure which resembles the outer envelope of the native virus antigenically and morphologically. The virus-like particles are formed in vitro upon expression, in a cell, of viral surface glycoprotein (GP) and a virion structural protein, VP40. It is also possible to produce VLPs by expressing only portions of GP and VP40 or by the addition of other viral proteins including the nucleoprotein, viral protein $(VP)_{24}$, VP30, and VP35. When the proteins used to produce a VLP are from different filoviruses or filovirus strains, hybrid VLPs are generated. VLPs can also be produced using more than one GP or VP40 from different filoviruses or filovirus strains.

The present invention generally relates to a novel method for producing VLP from filovirus, e.g., Ebola and Marburg virus. The method includes expressing viral glycoprotein GP and the virion structural protein, VP40 in cells. In one embodiment, the present invention relates to expression of GP and VP40 by transfection of DNA fragments which encode these proteins into the desired cells. Therefore, in a specific embodiment, the present invention relates to DNA fragments which encode any of the Ebola Zaire 1976 or 1995 (Mayinga isolate) GP and VP40 proteins. Accession# AY142960 contains the whole genome of Ebola Zaire, with individual genes including GP and VP40 specified in this entry, VP40 gene nucleotides 4479-5459, GP gene 6039-8068. The entire Marburg (strain Musoke) genome has been deposited in accession # NC_001608 for the entire genome, with individual genes specified in the entry, VP40 gene 4567-5478, GP gene 5940-7985, NP gene 103-2190. The protein ID for Ebola VP40 is AAN37506.1, for Ebola GP is AAN37507.1, for Marburg VP40 is CAA78116.1, and for Marburg GP is CAA78117.1. The DNA fragments were inserted into a mammalian expression vector, specifically, pWRG7077, and transfected into cells.

In another embodiment, the present invention relates to a recombinant DNA molecule that includes a vector and a DNA sequence as described above. The vector can take the form of a plasmid, a eukaryotic expression vector such as pcDNA3.1, pRcCMV2, pZeoSV2, or pCDM8, which are available from Invitrogen, or a virus vector such as baculovirus vectors, retrovirus vectors or adenovirus vectors, alphavirus vectors, and others known in the art. The minimum requirement is a promoter that is functional in mammalian cells for expressing the gene.

A suitable construct for use in the method of the present invention is pWRG7077 (4326 bp)(PowderJect Vaccines, Inc., Madison, Wis.). pWRG7077 includes a human cytomegalovirus (hCMV) immediate early promoter and a bovine growth hormone polyA addition site. Between the promoter and the polyA addition site is Intron A, a sequence that naturally occurs in conjunction with the hCMV IE promoter that has been demonstrated to increase transcription when present on an expression plasmid. Downstream from Intron A, and between Intron A and the polyA addition sequence, are unique cloning sites into which the desired DNA can be cloned. Also provided on pWRG7077 is a gene that confers bacterial host-cell resistance to kanamycin. Any of the fragments that encode Ebola GP, Ebola VP40, Marburg GP, and Marburg VP40 can be cloned into one of the cloning sites in pWRG7077, using methods known to the art.

All filoviruses have GP proteins that have similar structure, but with allelic variation. By allelic variation is meant a natural or synthetic change in one or more amino acids which occurs between different subtypes or strains of Ebola or Marburg virus and does not affect the antigenic properties of the protein. There are different strains of Ebola (Zaire 1976, Zaire 1995, Reston, Sudan, and Ivory Coast with 1-6 species under each strain). Marburg has species including Musoke, Ravn, Ozolin, Popp, Ratayczak, Voege, which have >78% homology between the different strains. It is reasonable to expect that similar VLPs from other filoviruses can be prepared by using the concept of the present invention described for MBGV and EBOV, i.e. expression of GP and VP40 genes from other filovirus strains would result in VLPs specific for those strains.

In a further embodiment, the present invention relates to host cells stably transformed or transfected with the above-described recombinant DNA constructs or expressing said DNA. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of the desired coding sequences when appropriate control sequences which are compatible with the designated host are used. Host cells include all cells susceptible to infection by filovirus.

Among prokaryotic hosts, *E. coli* is the most frequently used host cell for expression. General control sequences for prokaryotes include promoters and ribosome binding sites. Transfer vectors compatible with prokaryotic hosts are commonly derived from a plasmid containing genes conferring ampicillin and tetracycline resistance (for example, pBR322) or from the various pUC vectors, which also contain sequences conferring antibiotic resistance. These antibiotic resistance genes may be used to obtain successful transformants by selection on medium containing the appropriate antibiotics. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods.

In addition, the filovirus gene products can also be expressed in eukaryotic host cells such as yeast cells and mammalian cells. *Saccharomyces cerevisiae, Saccharomyces carlsbergensis,* and *Pichia pastoris* are the most commonly used yeast hosts. Control sequences for yeast vectors are known in the art. Mammalian cell lines available as hosts for expression of cloned genes are known in the art and include many immortalized cell lines available from the American Type Culture Collection (ATCC), such as HEPG-2, CHO cells, Vero cells, baby hamster kidney (BHK) cells and COS cells, to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences, poly A addition sequences, enhancer sequences which increase expression, or sequences which cause amplification of the gene. These sequences are known in the art.

The transformed or transfected host cells can be used as a source of DNA sequences described above. When the recombinant molecule takes the form of an expression system, the transformed or transfected cells can be used as a source of the VLP described below.

Cells may be transfected with one or more expression vector expressing filovirus GP and VP40 using any method known in the art, for example, calcium phosphate transfection as described in the examples. Any other method of introducing the DNA such that the encoded proteins are properly expressed can be used, such as viral infection, electroporation, to name a few.

For preparation of VLPs, supernatants are collected from the above-described transfected cells, preferably 60 hours post-transfection. Other times can be used depending on the desired number of intact VLPs. Our endpoint is the greatest number of intact VLPs, we could use other times which will depend on how we express the genes. Presumably an inducible system would not require the same length of incubation as transient transfections. The supernatants will undergo a low speed spin to reduce contamination from cellular material and then be concentrated by a high speed spin. The partially purified material is then separated on a 10-60% sucrose gradient. The isolation technique will depend upon factors such as the specific host cells used, concentration, whether VLPs remains intracellular or are secreted, among other factors. The isolated VLPs are about 95% pure with a low enough endotoxin content for use as a vaccine. In these instances, the VLP used will preferbly be at least 10-30% by weight, more preferably 50% by weight, and most preferably at least 70-90% by weight. Methods of determining VLP purity are well known and include SDS-PAGE densitometric methods.

The resulting VLPs are not homogeneous in size and exhibit conformational, neutralizing epitopes found on the surface of authentic Ebola or Marburg virions. The VLPs are comprised of one or more GP and one or more VP40. Other filovirus proteins can be added such as NP, VP24, VP30 and VP35 without affecting the structure.

While these results are novel and unexpected, based on the teachings of this application, one skilled in the art may achieve greater VLP yields by varying conditions of transfection and separation.

In another embodiment, the present invention relates to a single-component vaccine protective against filovirus. VLPs should be recognized by the body as immunogens but will be unable to replicate in the host due to the lack of appropriate viral genes, thus, they are promising as vaccine candidates. In a specific embodiment the filoviruses are MBGV and EBOV. A specific vaccine of the present invention comprises one or more VLP derived from cells expressing EBOV GP, VP40, and potentially NP, VP24, VP30 and/or VP35 for use as an Ebola vaccine, or VLP derived from cells expressing or MBGV GP, VP40, and potentially NP, VP24, VP30 and/or VP35 for use as a Marburg vaccine. Hybrid VLPs produced by mixing GP and VP40 from two or more filoviruses are another embodiment of the present invention. For example, a hybrid VLP can be produced using EBOV GP and Marburg VP40, or Marburg GP and EBOV VP40 as shown in the examples below. Even though the specific strains of EBOV and MBGV were used in the examples below, it is expected that protection would be afforded using VLPs from other MBGV strains and isolates, and/or other EBOV strains and isolates.

The present invention also relates to a method for providing immunity against MBGV and EBOV virus said method comprising administering one or more VLP to a subject such that a protective immune reaction is generated. When protection against more than one filovirus is desired, a panfilovirus vaccine can be prepared as is described in the Examples below. A panfilovirus vaccine can be prepared by mixing VLPs from different filoviruses, i.e. mixing eVLP and mVLP in a solution. Alternatively, a panfilovirus vaccine is comprised of one or more hybrid VLPs comprised of one or more GP or VP40, each from a different filovirus for which protection is desired.

Vaccine formulations of the present invention comprise an immunogenic amount of VLPs or a combination of VLPs as a panfilovirus vaccine, in combination with a pharmaceutically acceptable carrier. An "immunogenic amount" is an amount of the VLPs sufficient to evoke an immune response in the subject to which the vaccine is administered. An amount of from 0.1 or 1.0 mg or more VLPs per dose with one to four doses one month apart is suitable, depending upon the age and species of the subject being treated. Exemplary pharmaceutically acceptable carriers include, but are not limited to, sterile pyrogen-free water and sterile pyrogen-free physiological saline solution.

Administration of the VLPs disclosed herein may be carried out by any suitable means, including both parenteral injection (such as intraperitoneal, subcutaneous, or intramuscular injection), by in ovo injection in birds, orally and by topical application of the VLPs (typically carried in the pharmaceutical formulation) to an airway surface. Topical application of the VLPs to an airway surface can be carried out by intranasal administration (e.g. by use of dropper, swab, or inhaler which deposits a pharmaceutical formulation intranasally). Topical application of the VLPs to an airway surface can also be carried out by inhalation administration, such as by creating respirable particles of a pharmaceutical formulation (including both solid particles and liquid particles) containing the VLPs as an aerosol suspension, and then causing the subject to inhale the respirable particles. Methods and apparatus for administering respirable particles of pharmaceutical formulations are well known, and any conventional technique can be employed.

In another aspect of the invention, the VLPs can be produced in vivo. Using our established expression systems based on a mammalian expression vector (ex. pWRG7077), subjects can be administered by methods described above, with a single or multiple plasmids encoding VP40, GP, and potentially also NP, VP24, VP30, and VP35. The simultaneous administration with these expression vectors should induce in vivo formation of VLPs in the subject at the administration site in target cells within the skin such as epithelial cells, monocytes, and Langershans cells. Alternately, DNA encoding VP40, GP, and others could be introduced directly into cells, such as monocytes, dendritic or Langerhans cells, via electroporation and then the cells transferred back into the donor for administration. In this way, the donor cells would make VLPs within the donor and provide direct and efficient antigen presentation. These approaches allow efficient delivery of the antigens directly into vaccinees via plasmid DNA and may increase the overall immune responses, especially the T cell response following vaccination, compared to direct vaccination with standard VLP preparations The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

In a further embodiment, the present invention relates to a method of detecting the presence of antibodies against Ebola virus or Marburg virus in a sample. Using standard methodology well known in the art, a diagnostic assay can be constructed by coating on a surface (i.e. a solid support for example, a microtitration plate, a membrane (e.g. nitrocellulose membrane) or a dipstick, all or a unique portion of any of the Ebola or Marburg VLPs described above, and contacting it with the serum of a person or animal suspected of having an infection. The presence of a resulting complex formed between the VLPs and serum antibodies specific therefor can be detected by any of the known methods common in the art, such as fluorescent antibody spectroscopy or colorimetry. This method of detection can be used, for example, for the diagnosis of Ebola or Marburg infection and for determining the degree to which an individual has developed virus-specific Abs after administration of a vaccine.

In another embodiment, the present invention relates to a diagnostic kit which contains the VLPs described above and ancillary reagents that are well known in the art and that are suitable for use in detecting the presence of antibodies to Ebola or Marburg in serum or a tissue sample. Tissue samples contemplated can be from monkeys, humans, or other mammals.

In another embodiment, the present invention relates to a method for producing VLPs which have encapsulated therein a desired moiety.

The moieties that may be encapsulated in the VLP include therapeutic and diagnostic moieties, e.g., nucleic acid sequences, radionuclides, hormones, peptides, antiviral agents, antitumor agents, cell growth modulating agents, cell growth inhibitors, cytokines, antigens, toxins, etc. The moiety encapsulated should not adversely affect the VLP, or VLP stability. This may be determined by producing VLP containing the desired moiety and assessing its effects, if any, on VLP stability.

The subject VLP, which contain a desired moiety, upon administration to a desired host, should be taken up by cells normally infected by the particular filovirus, e.g., epithelial cells, keratinocytes, etc. thereby providing for the potential internalization of said moiety into these cells. This may facilitate the use of subject VLPs for therapy because it enables the delivery of a therapeutic agent(s) into a desired cell, site, e.g., a cervical cancer site. This may provide a highly selective means of delivering desired therapies to target cells.

In case of DNAs or RNAs, the encapsulated nucleic acid sequence can be up to 19 kilobases, the size of the particular filovirus. However, typically, the encapsulated sequences will be smaller, e.g., on the order of 1-2 kilobases. Typically, the nucleic acids will encode a desired polypeptide, e.g., therapeutic, such as an enzyme, hormone, growth factor, etc. This sequence will further be operably linked to sequences that facilitate the expression thereof in the targeted host cells.

In another embodiment, the present invention relates to a diagnostic assay for identifying agents which may cause disassembly of the VLP, or agents which can inhibit budding of virus from the host cell, or agents which inhibit filovirus entry into or exit from a cell. Such agents may include altered viral proteins, cellular factors, and chemical agents.

A diagnostic assay for agents which might inhibit viral budding comprises:
(i) contacting cells expressing VP40 and GP from a filovirus and producing VLPs with an agent thought to prevent viral budding from cells; and
(ii) monitoring the ability of said agent to inhibit VLP budding from cells by detecting an increase or decrease of VLPs in cell culture supernatant, wherein a decrease in VLPs in the supernatant indicates an inhibitory activity of said agent. This would include the generation of VLPs containing fluorescent tags attached to GP or VP40 to make the VLP generation trackable in high throughput screening assays.

A diagnostic assay for screening agents which inhibit viral entry into cells comprises:
(i) treating cells with an agent suspected of inhibiting viral entry;
(ii) contacting treated cells with filovirus VLPs;
(iii) detecting a change in the number of VLPs able to enter treated cells compared to untreated cells wherein a decrease in the number of VLPs in treated cells indicated an inhibitory activity of said agent. VLP entry into cells can be monitored using lipophilic dyes.

In another embodiment, the present invention relates to a diagnostic kit which contains cells expressing filovirus proteins GP and VP40 such that VLPs of said filovirus are produced and ancillary reagents suitable for use in detecting the presence of VLPs in the supernatant of said cells when cultured. Said cells would include any mammalian cell, for example, 293T, VERO, and other mammalian cells expressing VP40 and GP from Ebola virus or expressing VP40 and GP from Marburg virus.

Applicants for the first time have identified lipid rafts as a gateway for entry and exit from a cell. Stable lipid rafts serve as the site of filovirus assembly and budding. Therefore, in yet another embodiment of the invention, the present invention relates to a method for inhibiting entry of filovirus into cells, said method comprising inhibiting the association of the virus with lipid rafts in cells. Such methods would include providing a cell which produces filovirus VLP, administering a lipid rafts destabilizing agent, and monitoring the effect of the agent on filovirus entry by monitoring the amount of VLPs entering the cell as compared to a control of untreated cells, or alternatively, monitoring the effect of the agent on filovirus budding from the cell by monitoring the amount of VLPs in the culture supernatant as compared to a control of untreated cells.

Agents which destablitize lipid rafts include filipin, nystatin, and other cholesterol synthesis inhibitors known collectively as statins such as methyl-β-cyclodextrin, or agents which compete with the virus for binding to lipid rafts, such agents, including mutant VP40 or mutant GP, e.g. having mutations which inhibit palmitoylation at cystein residues 670 and 672.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods:

Plasmids, transfections, western blot, GM1 blot: cDNAs encoding Ebola-Zaire GP and VP40 as well as MBGV Musoke GP were cloned in pWRG7077 mammalian expression vector. 293 T cells were transfected using calcium phosphate transfection kit (Edge Biosystems, Gaithersburg, Md.) according to manufacturer's instructions. Western blot analysis was performed using as primary antibodies anit-EboGP mAb 13F6 (Wilson et al., 2000, Science 287, 1664), anti-Marburg GP mAb (5E2) (Dr. Michael Hevey, USAMRIID) anti Ebo-VP40 mAb (Dr. Connie Schmaljohn, USAMRIID) or a guinea pig anti-Marburg antibody (Dr. Michael Hevey, USAMRIID), followed by blotting with HRP-conjugated secondary antibodies and signals were detected by enhanced chemiluminescence. GM1 was detected in lysates or immunoprecipitates by spotting on a nitrocellulose membrane after boiling in SDS, followed by blocking of the membranes and blotting with HRP-conjugated CTB and detection by ECL.

Preparation of detergent insoluble fractions and lipid rafts: Lipid rafts were prepared after lysing the cells in lysis buffer containing 0.5% Triton-X100 as previously described (Aman and Ravishandran, 2000, supra). Raft and soluble fractions were then analyzed by immunoblotting. In some experiments (FIG. 3A), detergent-insoluble fraction was extracted without ultracentrifugation as described previously (Rousso et al., 2000, supra). Briefly, cells were pelleted and lysed in 0.5% Triton-X100 lysis buffer. After removing the lysate (soluble fraction), the pellet was washed extensively and SDS sample buffer added to pellet (insoluble fraction). Soluble and insoluble fractions were analyzed by SDS page and immunoblotting.

Cell culture, infections, virus and VLP purification: Peripheral blood mononuclear cells (PBMC) were isolated by density centrifugation through Ficoll-Paque (Amerhsam/Pharmacia, Piscataway, N.J.) according to manufacturer's instructions. PBMCs were cultured in RPMI/10% fetal bovine serum for 1 hour at 37° C., 5% $CO_2$ after which non-adherent cells were removed. Adherent cells were cultured for an additional 5 days. HEPG2 cells (ATCC, Manassas, Va.) were cultured to confluency with complete RPMI 1640 prior to use. Monocyte derived macrophages, HEPG2 cells, and Vero-E6 cells were infected at a multiplicity of infection (M.O.I.) of 1 with either Ebola-Zaire or Marburg Musoke virus for 50 minutes at 37° C., 5% $CO_2$. Non-adsorbed virus was removed from cells by washing monolayers twice with PBS followed by addition of fresh complete medium for an additional 24-48 hours. Purification and inactivation of Marburg virus was performed as previously described (Hevey et al., 1997, supra). Briefly, Vero-E6 cells were infected with MBGV and supernatant was harvested 6-7 days post-infection. The medium was clarified and virus concentrated by polyethylene glycol precipitation. After centrifugation at 10,000 g for 30 min, pellets were resuspended in Tris buffer and layered atop 20-60% sucrose gradients and centrifuged at 38,000 rpm for 4 hr. The visible virus band was collected. Samples were inactivated by irradiation ($10^7$ R, $^{60}$Co source) and tested for absence of infectivity in cell culture before use. For preparation of VLPs, supernatants were collected 60 h post-transfection, overlaid on 30% sucrose and ultracentrifuged at 26000 rpm for 2 hours. Pelleted particulate material was recovered in PBS and analyzed by immunoblotting or electron microscopy. As a further purification step, in some experiments this particulate material was loaded on a step gradient consisting of 80%, 40% and 30% sucrose. After 2 h centrifugation at 26000 rpm, the VLPs were recovered from the interface of 80% and 40% sucrose layers.

Plaque assays: Infectious Ebola and Marburg virions were enumerated using a standard plaque assay as previously described (Hevey et al., 1998, supra). Briefly, culture supernatants were serially diluted in EMEM. 100 ul of each dilution were added to wells of Vero-E6 cells in duplicate. Virus was allowed to adsorb for 50 minutes. Wells were then overlaid with 1×EBME and 0.5% agarose. Plates were incubated at 37° C., 5% $CO_2$ at which time a second overlay of 1×EBME/0.5% agarose and 20% neutral red was added to each well, incubated for additional 24 hours and plaques were counted.

Cell staining and confocal microscopy: 293T cells (human epithelial kidney cells, ATCC) were stained with indicated antibodies to viral proteins followed by Alexa-647 conjugated secondary antibodies (Molecular Probes, Eugene, Oreg.). Rafts were visualized by staining of GM1 with Alexa-488 conjugated CTB and in some experiments with rhodamin-conjugated CTB (FIG. 2B). Staining was performed on live cells on ice for 20 minutes. Cells were then washed with PBS, fixed in 3% paraformaldehyde, washed and mounted on microscopy slides. Images were collected using the BioRad (Hemel Hempstead, UK) Radiance 2000 system attached to a Nikon (Melville, N.Y.) E600 microscope. Alexa-488 immunostain was excited using 488 nm light from a Krypton-Argon laser and the emitted light was passed through an HQ515/30 filter. Fluorescence from the Alexa-647 dye was excited by 637 nm light from a red diode laser and collected after passing through an HQ660LP emission filter. The lasers were programmed to scan over successive focal planes (0.25-0.5 um intervals) at 50 lines per sec. Lasersharp software was used to control the confocal system and to reconstruct individual focal planes into 3-dimensional renderings.

Electron microscopy: Portions of particulate material were applied to 300-mesh, nickel electron microscopy grids precoated with formvar and carbon, treated with 1% glutaraldehyde in PBS for 10 min, rinsed in distilled water, and negatively stained with 1% uranyl acetate. For immunoelectron microscopy, fractions were processed as previously described for fluid specimens (Geisbert and Jahrling, 1995, Virus Res. 39, 129). Briefly, fractions were applied to grids and immersed for 45 min in dilutions of monoclonal antibodies against EBOV GP. Normal mouse ascetic fluid was tested in parallel. Grids were washed with the TRIS buffer and incubated for 45 min with goat anti-mouse IgG labeled with 10 nm gold spheres (Ted Pella Inc. Redding, Calif.). Grids were washed in PBS, and fixed in 1% glutaraldehyde. After fixation, grids were rinsed in drops of distilled water and negatively stained with 1% uranyl acetate. For pre-embedment staining, cells were stained with anti-Ebola GP mAb followed by gold-anti-mouse Ab, fixed with 2% glutaraldehyde in Millonig's buffer (pH7.4) for 1 h and post-fixed in 1% uranylacetate, dehydrated and embedded in POLY/BED 812 resin (Polysciences, Warrington, Pa.). Resin was allowed to polymerize for 16 h at 60° C., Ultrathin sections (~80 nm) were cut, placed on 200-mesh copper electron microscopy grids and negatively stained. Stained grids were examined with a JEOL 1200 EX transmission electron microscope at 80 kV.

Virus and cells. MARV or EBOV were propagated and enumerated by plaque assay on Vero E6 cells. MARV Musoke or EBOV Zaire 1995 virus preparations were purified over a continuous sucrose gradient and inactivated (i) by irradiation with $1\times10^7$ rads, as previously described (Hevey et al., 1997, Virology, 239, 206-216). Guinea pig-adapted strains of EBOV Zaire 1995 or MARV Musoke were used to challenge vaccinated guinea pigs (Hart, M. K. 2003, supra; Sullivan et al., 2003, Nature 424, 681-4; Sullivan et al., 2000, Nature 408, 605-9). MARV or EBOV-infected cells and guinea pigs were handled under maximum containment in a biosafety level (BSL)-4 laboratory at the United States Army Medical Research Institute of Infectious Diseases. Convalescent serum samples removed from the BSL-4 laboratory were gamma-irradiated with $2\times10^6$ rads from a $^{60}$Co source before analysis in BSL-2 or 3 laboratories (Hevey et al., 1998, Virology 251, 28-37; Bavari et al, 2002, J. Exp. Med. 195, 593-602).

Mice. β/T cell receptor (α/β and γ/δ T cell)-deficient or IFN-γ-deficient mice were obtained from Jackson Laboratories (Bar Harbor, Me.). Jh B cell-, CD4+ T cell-, 2m- or perform-deficient mice were purchased from Taconic (Germantown, N.Y.). Wild-type C57B1/6 or BALB/c mice were obtained from National Cancer Institute, Frederick Cancer Research and Development Center (Frederick, Md.). All mice were 8-10 weeks old at the start of the experiment, both female and male mice were used, and mice were randomly divided into treatment groups. Mice were housed in microisolator cages and provided autoclaved water and chow ad libitum. Mice were challenged by intraperitoneal injection with 1000 pfu (~30,000 $LD_{50}$) of mouse-adapted EBOV diluted in phosphate buffered saline (PBS). After challenge, mice were observed at least twice daily for illness. VLP production for vaccine experiments. VLPs for vaccine assays were prepared essentially as previously described, with minor modifications (Bavari et al., 2002, supra; Warfield et al., 2003, Proc. Natl. Acad. Sci. USA 100, 15889-94; Swenson et al., 2004, FEMS Immunol. Med. Microbiol., 40, 27-31). To generate mVLPs or eVLPs, 293T cells were co-transfected with pWRG vectors encoding for MARV or EBOV VP40 and GP using Lipofectamine 2000 (Invitrogen, Carlsbad, Calif.). To purify the VLPs, the cell supernatants were cleared from cellular debris and subsequently pelleted at 9,500×g for 4 hr in a Sorvall GSA rotor. The crude VLP preparations were then separated on a 20-60% continuous sucrose gradient centrifuged in a SW41 rotor at 38,000 rpm for 18 hr (Beckman-Coulter, Inc., Fullerton, Calif.). The VLPs were concentrated by a second centrifugation and resuspended in endotoxin-free phosphate-buffered saline (PBS). The gradient fractions containing the VLPs were determined by western blots and electron microscopy. The mVLPs routinely sedimented in ~35-50% sucrose, while the eVLPs sedimented in ~30-40% sucrose. Total protein concentrations of the VLP preparations were determined after lysis in NP40 detergent using a detergent-compatible protein assay (BioRad, Hercules, Calif.). The endotoxin levels in all VLP preparations used in this study were <0.03 endotoxin units by the *Limulus amebocyte* lysate test (Biowhittaker, Walkersville, Md.). In some cases, the VLPs were inactivated by irradiation with $1\times10^7$ rads, as previously described (Hart, M. K. 2003, supra).

Mouse vaccinations. Mice were vaccinated intramuscularly with 10-100 ug of eVLPs alone or mixed with 10 ug of QS-21 adjuvant (kindly provided by Antigenics, Inc., Lexington, Mass.) diluted in endotoxin-free PBS twice at 3-week intervals. Control mice were vaccinated on the same schedule with 10 ug of QS-21 adjuvant in PBS or PBS alone. Mice were challenged with EBOV 6 weeks after the second vaccination.

Guinea pig vaccinations and filovirus challenge. Inbred strain 13 guinea pigs (USAMRIID, Frederick, Md.) were randomized into groups and each guinea pig was identified using a radio-transponder microchip (BioMedic Data Systems, Inc., Seaford, Del.) inserted underneath the skin. Guinea pigs were vaccinated intramuscularly with 50 μg of mVLPs (n=5), eVLPs (n=5), or iMARV (n=5) with 200 μl of RIBI monophosphoryl lipid+synthetic trehalose dicorynomycolate+cell wall skeleton emulsion (Corixa Corporation, Hamilton, Mont.) or 10 ug of the saponin derivative QS-21 (Antigenics, Lexington, Mass.) diluted in endotoxin-free PBS on days 0, 21, and 42. Control guinea pigs were vaccinated with RIBI adjuvant in PBS alone (n=6). Serum samples were obtained from each guinea pig immediately before each vaccination and immediately prior to challenge (days 0, 21, 42, and 72). In another set of experiments, guinea pigs were vaccinated once intramuscularly with 100 μg of eVLPs, mVLPs, hybrid VLPs, or 100 μg of both eVLP and mVLPs in 200 μl of RIBI monophosphoryl lipid+synthetic trehalose dicorynomycolate+cell wall skeleton emulsion (Corixa Corporation, Hamilton, Mont.) diluted in endotoxin-free PBS. Control guinea pigs were vaccinated with RIBI adjuvant in PBS alone. The guinea pigs were challenged subcutaneously 28-30 days after vaccination with ~1000 pfu [2,000 50% lethal doses ($LD_{50}$)] of guinea pig-adapted MARV or EBOV diluted in PBS (Hevey, M. 1997, supra; Connolly B M, 1999, 179 Suppl 1, 203-17). After challenge, guinea pigs were observed at least twice daily for illness. Serum viremia was determined on day 7 by standard plaque assay, as previously described (Swenson et al., 2004, supra). Vaccine experiments to test protective efficacy were performed twice. Research was conducted in compliance with the Animal Welfare Act and other federal statutes and regulations relating to animals and experiments involving animals and adhered to principles stated in the Guide for the Care and Use of Laboratory Animals, National Research Council, 1996. The facility where this research was conducted is fully accredited by the Association for Assessment and Accreditation of Laboratory Animal Care International.

Antibody titers. Levels of MARV and EBOV-specific antibodies were determined, as previously described (Hevey et al., 1997, supra). Briefly, the wells were coated with sucrose-purified inactivated MARV or EBOV virions. Serial dilutions of each serum sample were tested and the endpoint titers were determined as the inverse of the last dilution where the optical density of the sample was 0.2 greater than control wells (irrelevant heterologous antigen or wells without antigen). Convalescent serum samples were removed from the BSL-4 laboratory after gamma-irradiation with $2\times10^6$ rads from a $^{60}$Co source.

Proliferation assay. Single-cell suspensions were generated from the spleens of individual, fully-vaccinated guinea pigs in RPMI-1640 medium containing 10% fetal bovine serum, 2 mM L-glutamine, 1 mM HEPES, and 0.1 mM non-essential amino acids. As indicated, splenocytes were depleted of $CD4^+$ or $CD8^+$ cells by negative selection using mouse anti-guinea pig CD4 or CD8 (Research Diagnostics, Inc., Flanders, N.J.) and anti-mouse IgG magnetic beads (Dynal Biotech, Inc, Lake Success, N.Y.). The total splenocytes or splenocytes depleted of $CD4^+$ or $CD8^+$ T cells were plated in 96-well culture plates at 200,000 cells per well in complete RPMI alone or with 10 μg/ml of eVLP or mVLP, as indicated. On day 5, 1 μCi of $^3$H-thymidine was added to each well and the amount of $^3$H incorporation was determined.

Plaque Reduction-Neutralization Assay.

To test for the presence of plaque-neutralizing antibodies, threefold dilutions of guinea pig sera were incubated with ~100 pfu of MARV or EBOV at 37° C. for 1 hr in the presence of 5% guinea pig serum as a source of complement. The antibody-virus mixtures were then added to confluent Vero E6 cells and a standard plaque assay with Vero E6 cells was performed (Hevey et al., 1997, supra). The percent of plaque reduction was calculated by comparing the number of pfu present in each sample to the pfu obtained with virus alone (Hevey et al., 1997, supra; Takada et al., 2003, J. Virol. 77, 1069-74). The data are displayed as the 80% plaque reduction-neutralization titer ($PRNT_{80}$), which is defined as the inverse of the last dilution where >80% inhibition of virus infection is observed.

Statistical Analysis.

The proportion of treated and control animals surviving was compared by two-tailed Fisher exact tests within groups. The adjustments for multiple comparisons were made by stepdown Bonferroni correction. Analyses were conducted using SAS Version 8.2 (SAS Institute Inc., SAS OnlineDoc, Version 8, Cary, N. C. 2000). A ρ value of 0.05 was considered significant.

EXAMPLE 1

Association of Filovirus Glycoproteins with Lipid Rafts.

Figure 2A:
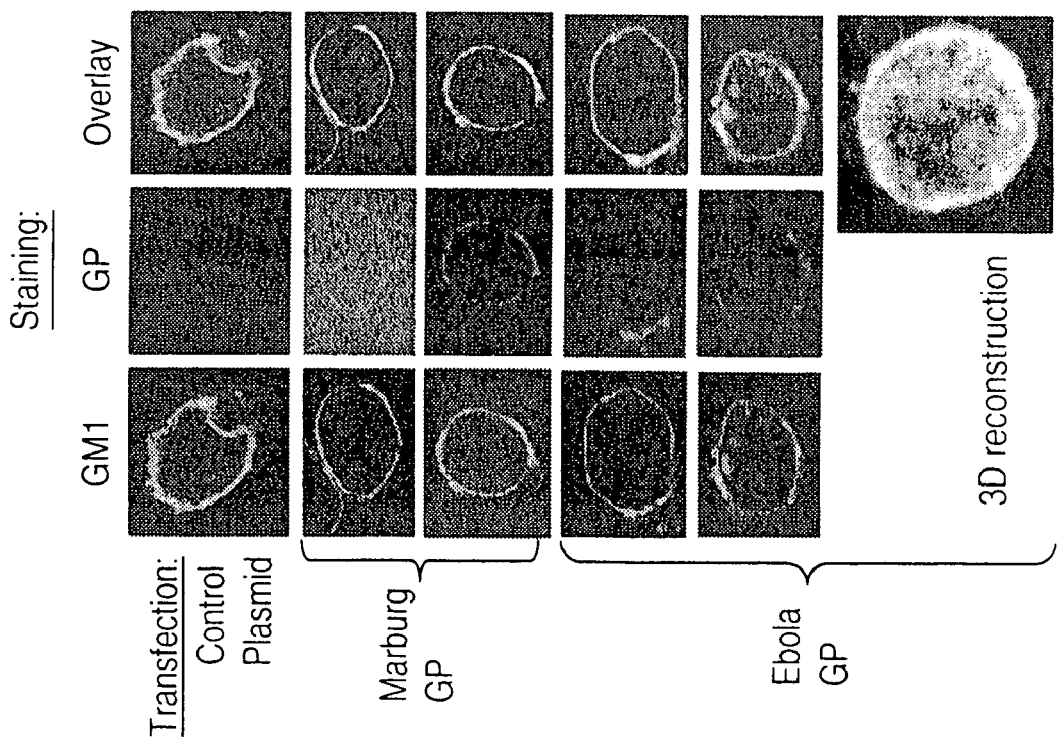

Targeting of membrane-spanning proteins to lipid rafts is commonly governed by dual acylation of cysteine residues at the cytosolic end of the transmembrane domains (Rousso et al, 2000, supra; Zhang et al., 1998, Immunity 9, 239). The filovirus envelope glycoproteins (GP) contain such acylation signals in their transmembrane domains (Feldmann and Klenk, 1996, supra) and palmitoylation of Ebola GP has been recently reported (Ito et al., 2001, J. virol. 75, 1576). By transient expression of the filovirus envelope glycoproteins in 293T cells and subsequent extraction of rafts by sucrose gradient ultracentrifugation (Aman and Ravichandran, 2000, supra), we examined whether these glycoproteins localize to lipid rafts. As shown in FIG. 1 (A and B), a significant fraction of Ebola and Marburg GPs were found to reside in rafts. In contrast, an Ebola GP, mutated at cysteine residues 670 and 672 ($EbO-GP_{C670/672A}$), the putative palmitoylation sites, failed to localize to the rafts (FIG. 1B). Lipid rafts are highly enriched in ganglioside M1 (GM1) which can be detected by its specific binding to cholera toxin B (CTB) (Harder et al., 1998, J. Cell biol. 141, 929; Heyningen, S. V., 1974, Science 183, 656). As a control for the quality of raft preparations, we analyzed the soluble and raft fractions for the presence of GM1 by spot blots using HRP-conjugated CTB and demonstrated that GM1 was exclusively found in the raft fractions (FIGS. 1A and B, lower panels). The association of GP with detergent insoluble fraction was dependent on cholesterol since pre-treatment with methyl-β-cyclodextrin (MβCD), a drug that depletes the membrane from cholesterol (Christian et al., 1997, J. Lipid Res. 38, 2264), resulted in almost complete removal of Ebola GP from rafts (FIG. 1C, upper panel). As a further control, we showed that transferrin receptor (TrfR), a molecule excluded from rafts (Harder et al., 1998, supra), was only found in the soluble fraction (FIG. 1C, lower panel). To confirm the raft localization of Ebola and Marburg GP on intact cells, we also performed confocal laser microscopy on 293T cells that were transfected with Ebola or Marburg GP and co-stained with anti-GP antibodies and CTB. As shown in FIG. 2A, a substantial portion of both of the glycoproteins were found to colocalize with GM1 in large patches on the plasma membrane, confirming the raft association of both glycoproteins on intact cells. Movies visualizing 25 sections through the cells, as well as three-dimensional (3-D) reconstruction of the cells by compiling data from these sections are available as supplemental data on the web (web movies 1 and 2). Confocal microscopy again showed that the membrane domains visualized by CTB staining were devoid of the raft excluded TrfR (FIG. 2B).

EXAMPLE 2

Filoviral Proteins Associate with Lipid Rafts in Cells Infected with Live Virus.

Two of the primary target cells of filoviruses are monocyte/macrophages and hepatocytes (Feldman and Klenk, 1996, supra). Thus, to examine the localization of EBOV and MBGV proteins with respect to lipid rafts during infection with live virus, primary human monocytes, HepG2 hepatocytes, and also Vero-E6 cells (commonly used to propagate filoviruses) were used as target cells. Human monocytes were infected with the Musoke strain of MBGV, after 24 h detergent-insoluble and detergent-soluble fractions were separated by centrifugation (Rousso et al., 2000, supra). As shown in FIG. 3A, a major fraction of viral proteins was detected in the detergent-insoluble fraction (I) 24 hours after infection. We then performed similar experiments with HepG2 cells, infected with EBOV-Zaire95 and prepared lipid rafts by sucrose gradient ultracentrifugation. Similar to Marburg, Ebola VP40 and GP were detected mainly in lipid rafts 24 h after infection of HepG2 hepatocytes (FIG. 3B). To further confirm the accumulation of filovirus proteins in lipid rafts in intact cells, Vero-E6 cells, infected with EBOV, were fixed, irradiated and costained with anti-Ebola antibody and CTB. As shown in FIG. 3C, we observed a striking colocalization of viral proteins with the lipid rafts in intact Ebola-infected cells (see also web movies 5 and 6), suggesting that viral proteins assemble at lipid rafts during the course of viral replication.

EXAMPLE 3

Ebola and Marburg Virions Incorporate the Raft Molecule GM1 During Budding

Figure 4B:
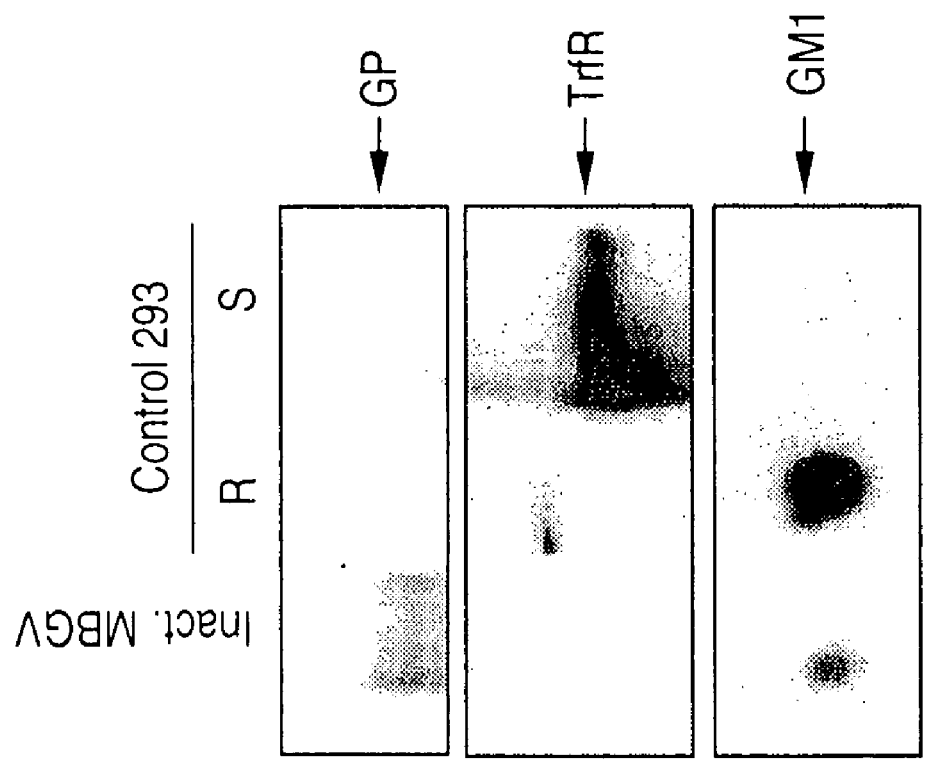
FIGS. 4A and 4B. Incorporation of GM1 in released filovirus virions. (A). Ebola virus was immunoprecipitated from supernatant of infected Vero-E6 cells (lane 2), or uninfected cells as control (lane 1), using anti-GP mAb. After irradiation ($2 \times 10^6$ R), a fraction of immunoprecipitate (IP) was spotted on nitrocellulose membrane and blotted with HRP-conjugated CTB to detect GM1 (lower panel). Another portion of the IP was analyzed by SDS-PAGE and immunoblotting with anti-GP mAb (top panel). (B) MBGV (1 mg), prepared by ultracentrifugation and inactivated by radiation ($1 \times 10^7$ R), was analyzed for the presence of GM1, TrfR and GP in a similar fashion. As control, rafts and soluble fractions from untransfected 293T cells were used.
Figure 4A:
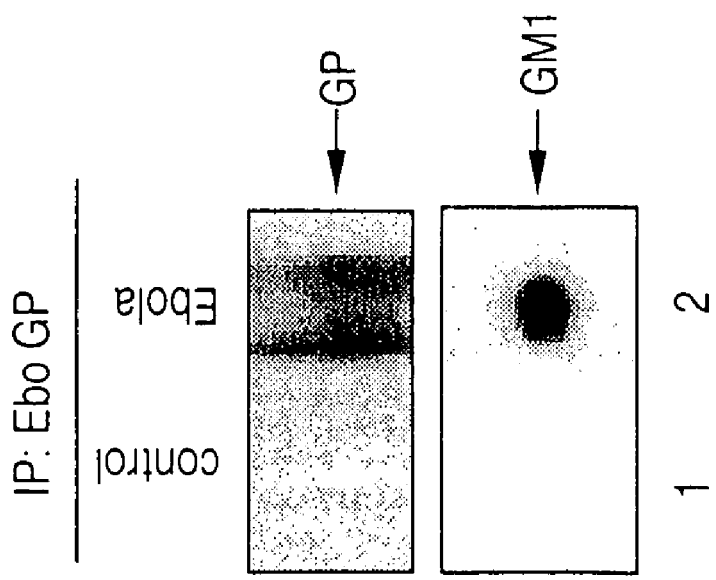

To determine whether the virus was released through lipid rafts, we analyzed EBOV from culture supernatants of infected cells for the presence of the raft marker GM1. Enveloped viruses bud as virions surrounded by the portion of the plasma membrane at which assembly takes place (Simons and Garoff, 1980, J. Gen. Virol. 50, 1). Release of virions through lipid rafts would therefore result in incorporation of raft-associated molecules in the viral envelope, thus identifying virus budding from the rafts. As shown in FIG. 4A, EBOV immunoprecipitated with anti-Ebola GP antibody from supernatant of infected Vero-E6 cells contained readily detectable levels of GM1. We also analyzed inactivated Marburg virus that had been purified by ultracentrifugation for the incorporation of GM1 and demonstrated that GM1 was detectable in MBGV (FIG. 4B, lower panel). In contrast, the raft-excluded protein TrfR was not incorporated in Marburg virions (FIG. 4B, middle panel). Taken together, these data strongly suggested that both viruses exit cells through lipid rafts.

EXAMPLE 4

Release of GM1-Containing Particles by Ectopic Expression of Ebola Proteins

To further test the hypothesis that filoviruses assemble and bud via lipid rafts, we transiently expressed viral proteins and searched for GM1-containing virus-like particles (VLPs). Several viral proteins have been shown to support the formation of VLPs (Porter et al., 1996, J. Virol. 70, 2643; Delchamber et al., 1989, EMBO J. 8, 2753; Thomsen et al., 1992, J. Gen. Virol. 73, 1819). In transfected 293T cells, Ebola GPwt, $GP_{C670/672A}$ and VP40 were readily detected in cell lysates when each protein was expressed individually (FIG. 5A, panels 1 and 3; lanes 2,3,4). However, when VP40 and GP were coexpressed, little GP and almost no VP40 were found associated with the cells 60 hours after transfection (FIG. 5A, panels 1 and 3; lane 5). To examine the viral proteins released from the cells, culture supernatants were cleared of cells, and particulate material was purified by ultracentrifugation over a 30% sucrose cushion. As shown in FIG. 5A (panels 2 and 4; lanes 2-4), large amounts of GPwt and lesser quantities of $GP_{C670/672A}$ or VP40 were detected in the particulate material from the supernatants of singly transfected cells. Interestingly, coexpression of GPwt and VP40, directed the majority of both proteins into the supernatant (FIG. 5A, panels 2 and 4, lane 5). Next, we tested if the released particles incorporated the raft-associated molecule GM1. Anti-Ebo-GP immunoprecipitates from the supernatants of the cells transfected with GPwt or GPwt+VP40, but not $GP_{C670/672A}$, contained GM1 (FIG. 5A, panel 5), suggesting that the release of these particles takes place through the rafts. We performed a second step of purification on these particles using a sucrose step gradient to separate the virus-like particles from the cell debris. The low density fraction floating between 40% and 80% sucrose was then analyzed by Western blot. As shown in FIG. 5B, these particles contained GM1 but totally excluded transferrin receptor, further confirming the release of particles through lipid rafts.

EXAMPLE 5

Particles Formed by EBOV GP and VP40 Display the Morphological Characteristics of Ebola Virus We determined the composition and morphology of these particles by examination of the purified particulate material using electron microscopy. Interestingly, most of the particles obtained from the supernatants of the cells cotransfected with GPwt and VP40 displayed a filamentous morphology strikingly similar to filoviruses (FIGS. 6A and B) (Geisbert and Jahrling, 1995, supra; Murphy et al., 1978, *Ebola and Marburg virus morphology and taxonomy*. 1st edition. S. R. Pattyn, editor. Elsevier, Amsterdam, pp. 1-61). In contrast, the material obtained from cells transfected with GPwt, $GP_{C670/672A}$ or VP40 only contained small quantities of membrane fragments, likely released during cell death (data not shown). The virus-like particles (VLPs) generated by GP and VP40 were released at a high efficiency. Typically, we achieve a titer of 0.5-1.0×10$^6$ VLPs/ml 2-3 days after transfection. The VLPs have a diameter of 50-70 nm and are 1-2 um in length (FIG. 6). This is similar to the length range of Ebola virions found in cell culture supernatants after in vitro infection (Geisbert and Jahrling, 1995, supra). The shorter diameter of VLPs (as compared to 80 nm for EBOV) may be due to the lack of ribonucleoprotein complex. We observed all types of morphologies described for filoviruses such as branched, rod-, U- and 6-shaped forms (Feldman and Klenk, 1996, supra; Geisbert and Jahrling, 1995, supra) among these particles (FIG. 6). In addition, the VLPs were coated with 5-10 nm surface projections or "spikes" (FIG. 6), characteristic for EBOV (Feldman and Klenk, 1996, supra; Geisbert and Jahrling, 1995, supra). Immunogold staining of the VLPs with anti-Ebola GP antibodies demonstrated the identity of the spikes on the surface of the particles as Ebola glycoprotein (FIG. 6B). To visualize the process of the release of the VLPs, cells transfected with GP and VP40 were analyzed by electron microscopy after pre-embedment immunogold staining. FIG. 6C shows a typical site of VLP release, where a large number of particles that stain for GP exit through a small region of the plasma membrane (indicated by arrows). These sites of VLP release have an average diameter of about 1 um. Given the incorporation of GM1 in the VLPs (FIG. 5) these particle-releasing platforms most likely represent coalesced lipid raft domains.

EXAMPLE 6

Entry of EBOV is Dependent on the Integrity of Lipid Rafts.

Having established a critical role for lipid rafts in virus release, we sought to investigate if filoviruses utilize the same gateway for entry. To examine the role of lipid rafts in filovirus entry, the effects of raft-disrupting agents filipin and nystatin on Ebola infection were explored. Brief treatment of cells with filipin (0.2 ug/ml, 30 minutes) prior to infection resulted in a significant inhibition of EBOV infection evident by reduced viral titer 48 hour post infection (FIG. 7). Similar results were also obtained with another cholesterol-destabilizing agent nystatin (FIG. 7). This effect was not due to a general cytotoxic effect by the drugs as cells were shown to be viable by trypan blue exclusion (data not shown). To rule out the possibility of a persistent effect of this brief drug treatment on the viral replication, we let an aliquot of the cells recover in medium (for 4 h) after filipin treatment before infecting them with EBOV. As shown in FIG. 7 (Filipin recovery), these cells could produce large amounts of virus, ruling out the possibility of late effects of the drug on viral replication. In fact, in cells recovered from raft disruption the infection was even more efficient. This might be due to a synchronizing effect by reorganization of the microdomains resulting in a more efficient entry of the virus into a larger number of cells. We also considered the possibility that raft disruption may interfere with virus attachment rather than entry. However, titering of the virus recovered after the 50 minute binding showed that same amount of EBOV had bound to both treated and control cells (data not shown). Taken together, these data suggest that lipid rafts play a critical role in the entry stage of Ebola infection.

EXAMPLE 7

Marburg VLP Production.

While both EBOV and MBGV appear to utilize the localization within lipid raft microdomains for viral assembly, other differences seem to exist between the two viruses in their replication mechanism. Ebola VP40 has been reported to be mainly localized to the plasma membrane (Ruigrok et al, 2000, J. Mol. Biol., 300(1):103-12) whereas Marburg VP40 has been shown to associate with late endosomes and multivesicular bodies (Kolesnikova et al, 2002, J. Virol. 76(4): 1825-38). Thus, it was not entirely clear whether VLPs could be formed in a similar manner for MBGV and if they would retain similar structure and morphology to the live virus.

In order to assess the ability of MBGV proteins to form VLPs, 293T cells were transfected with cDNAs encoding MBGV-Musoke GP as well as VP40 using lipofectamin-2000 according to manufacturer's instructions (Invitrogen, Carlsbad, Calif.). Cell supernatants were harvested after 48 h and subjected to immunoprecipitation with mAb to Marburg GP and anti-mouse coated magnetic beads (Dynal, Lake Success, N.Y.). Immunoprecipitates were washed with PBS and analyzed by immunoblotting. VP40 was coimmunoprecipitated with GP in supernatants of cells transfected with both GP and VP40 (data not shown), suggesting that both proteins are released in a complex. The particulate materials was purified from the supernatants by sucrose gradient ultracentrifugation as described. Particulate material recovered from both the 10/40% and 40/60% interfaces was analyzed by Western blot using MBGV anti-GP and anti-VP40 specific antibodies. Western blot analysis indicates the presence of both viral proteins found in the 40% and 60% VLP fractions, suggesting that particles containing the viral proteins have a broad range of density (data not shown).

To determine if this particulate material in fact contains VLPs we analyzed the particles by electron microscopy. Structures similar to live virus were seen in both the 40% or 60% sucrose fractions purified from supernatants of GP/VP40 expressing cells. Immunogold staining of the VLPs with MBGV anti-GP antibodies indicated the presence of glycoprotein spikes on the surface of the particles. Taken together these data clearly indicate that, similar to Ebola virus, VLPs can be generated by coexpression of Marburg virus matrix and glycoproteins.

While in the case of HIV the raft localization is governed by myristylation of the matrix protein gag, no such signals are present in filoviral VP40. In contrast, raft localization of filoviral proteins seems to be driven by the glycoprotein that contains two palmitoylation sites at the end of its transmembrane domain (Ito et al., 2001, J. Virol. 75(3):1576-80). These sites are essential for both raft localization as well as VLP release. The requirement for co-expression of GP for efficient release of VLPs suggests that GP may be facilitating this process by recruiting the assembly complex into raft microdomains. However, it is possible that other structural elements in GP, beside raft association signals, are also needed for the proper coordination of VP40 molecules to form the filamentous structure. VLPs represent an excellent safe and surrogate model for such structure function studies.

The addition of a vector encoding the nucleoprotein NP to the original transfection protocol also produces VLPs in a similar manner to GP+VP40. The sequence of Marburg NP is deposited in accession # NC_001608 with protein ID number: 042025.1. Western blot analysis of VLPs and immunoprecipitations confirm the presence of NP (data not shown). This suggests co-association of the proteins indicating the potential for filovirus like structures. This indicates that additional MGBV proteins may be incorporated into the structure thereby expanding the viral proteins which may serve as immunogens.

EXAMPLE 8

Contribution of NP and other viral proteins to VLP release. We and others have shown that the presence of GP increases the efficiency of VP40 vesicular release (Bavari et al., 2002, supra; Noda et al., 2002, J. Virol. 76, 4855-65). Licata et al. (2004, J. Virol. 78, 7344-51) also reported that coexpression of nucleoprotein (NP) further increases VLP production and release in VP40 expressing cells. To evaluate the contribution of NP and other viral proteins to VLP release, 293T cells were transfected with various combinations of GP, VP40, and NP, and cells and supernatants were harvested 48 hours after transfection. VLPs were measured in cellular lysates and cell culture supernatants. Our results indicate that GP and NP, when individually transfected with VP40, increased VLP production to about three fold and cotransfection of all three plasmids further augmented the VLP release by up to 5-6 fold. Electron microscopy analysis of the supernatants of cells transfected with the three plasmids displayed large number of filamentous structures.

The nucleocapsid of EBOV consists of a complex of NP, L, VP35, and VP30 that encompass the RNA genome (Feldman and Kiley, 1999, Curr. Top. Microbiol. Immunol. 235, 1-21). It has been reported that VP35 and NP when expressed in presence of VP24 are sufficient for the formation of filamentous particles (Huang et al., 2002, Mol. Cell 10, 307-16). Therefore, it was possible that coexpression of nucleocapsid components may improve the VLP release. We first examined the effects of VP35, VP30, and VP24 on VP40 VLP release and found that none of these proteins had any significant effect on VLP production when transfected with VP40 alone (data not shown). However, when these plasmids were cotransfected with GP, VP40 and NP, there was a significant increase in VLP production. While VP24 alone had only a minor effect on VLP release, VP30 and VP35 increased VLP production by about 50% and 130-150% respectively. Combining VP30, VP24, or both with VP35 did not significantly change the efficiency of VLP release. Since the presence of nucleocapsid components clearly enhanced the VLP release we also asked the question whether the presence of negative strand RNA with EBOV flanking sequences would further increase VLP release. For this purpose, we used a recently reported RNA polymerase I (Pol-I) based minigenome plasmid (Groseth et al., in press). Expression of this plasmid results in a Pol-1 transcript with EBOV leader and trailer sequences in viral RNA orientation that can be packaged into viral particles. However, repeated experiments did not demonstrate any significant change in the level of VLP release upon expression of the minigenome, suggesting that the nucleocapsid structures that contribute to VLP release are stable in the absence of packageable RNA. Taken together these finding indicate that the nucleocapsid proteins NP, VP30, and VP35 can significantly enhance the release of Ebola virus-like particles and may also enhance the stability of the structures.

EXAMPLE 9

Immunogenicity in Mice.

The glycoprotein of filoviruses is the only protein expressed on the viral surface and is believed to be the main immunogenic determinant (Feldman and Klenk, 1996, supra). Delivery of Ebola GP as a DNA vaccine has been shown to protect mice from lethal challenge (Vanderzanden et al, 1998, Virology 246(1):134-44). Adenovirus mediated gene transfer of Ebola GP was also protective in non-human primates (Sullivan N. J. et al, 2000, Nature, 408(6812):605-9; Sullivan N. J. et al, 2003, Nature, 424(6949):681-4.). In addition, VP40 can provide some level of protective immune response in certain mouse strains (Wilson et al, Virology. 2001 286(2):384-90). The filovirus like particles express both GP and VP40 in a filamentous structure strikingly similar to authentic viruses. These properties suggest that VLPs may be excellent vaccine candidates. Several other VLPs have been shown to be capable of triggering both arms of the immune system and protect against live virus challenge (Furumoto et al, 2002, J Med Invest. 49(3-4):124-33; Peters BS: Vaccine. 2001, 20(5-6):688-705). Therefore, we sought to examine the immunogenicity of eVLPs and mVLPs.

eVLPs protect mice against challenge with mouse-adapted EBOV. To assess whether the eVLPs made of VP40 and GP could induce protection against infection with Ebola, mice were immunized three times intraperitoneally with 40 ug of VLPs and then challenged with mouse-adapted Ebola virus 3 weeks following the last immunization. Mice immunized with EBOV VLPs developed high titers of EBOV-specific antibodies, as determined by ELISA (FIG. 8a). Additionally, serum from EBOV VLP-immunized mice was able to neutralize EBOV infection of VeroE6 cells (FIG. 8b). Following challenge with 300 pfu of EBOV, ten of ten mice immunized with EBOV VLPs survived, while mice immunized with inactivated EBOV or MBGV had only low survival (FIG. 9). One of ten naïve mice survived following EBOV challenge (FIG. 9). The viral load of the VLP-immunized mice (n=10) was 20±42 pfu at 7 days following challenge.

Discussion

These results demonstrate that filoviruses utilize lipid rafts as a platform for budding from the cells. We documented this phenomenon in reconstruction experiments and in the process of live virus infections. Both after transient expression of filovirus glycoproteins as well as in EBOV and MBGV infected cells, we observed large patches of envelope glycoproteins in association with lipid rafts (FIGS. 1, 2, and 3). Our results also demonstrate that the released virions incorporate the raft-associated molecule GM1, but not transferrin receptor, a protein excluded from lipid rafts (Harder et al., 1998, supra). Using electron microscopy on cells transfected with Ebola GP and matrix protein VP40, we also demonstrate the site of release of Ebola-like particles to be localized in a small area of the plasma membrane about 1 um wide (FIG. 6C). Therefore, such patches of rafts appear to represent the site of filovirus assembly and budding. Electron microscopic studies show that virus budding at the plasma membrane requires an accumulation of viral components including nucleocapsid, matrix and envelope glycoprotein in an orchestrated manner, concurrent with structural changes in the plasma membrane (Dubois-Delcq and Reese, 1975, J. Cell Biol. 67, 551). This process is dependent on a precise coordination of the involved components (Garoff et al., 1998, Microbiol. Mol. Biol. Rev. 62, 1171). Thus, compartmentalization of viral assembly in a specialized microdomain, such as rafts, with its ordered architecture and selective array of molecules may increase the efficiency of virus budding and decrease the frequency of release of defective, non-infectious particles.

Besides acting as a coordination site for viral assembly, rafts may have a profound impact on viral pathogenicity as well as host immune response to viruses. Transfer of the incorporated molecules with signaling capabilities into newly infected cells may affect the intracellular biochemical processes in favor of a more efficient viral replication. Furthermore, selective enrichment of certain proteins such as adhesion molecules can affect the efficiency of viral entry and possibly virus tropism. Incorporation of GPI-anchored proteins in the viral envelope such as inhibitors of complement pathway CD55 and CD59, which have been detected in HIV virions (Saifuddin et al., 1997, J. Gen. Virol. 78, 1907), may help the virus evade the complement-mediated lysis.

An important aspect of our study is the generation of genome-free filovirus-like particles. Our biochemical data show that the VLPs incorporate both Ebola GP and matrix protein VP40, as well as raft-associated ganglioside M1, similar to the results obtained with live virus infections (FIG. 4). A striking morphological similarity between these VLPs and live filoviruses was observed in electron microscopic studies (FIG. 6). These findings have several important implications. While several viral matrix proteins support the formation of VLPs, Ebola VP40 seems to be unique in that it requires the expression of envelope glycoprotein for efficient formation of particles. Recently, Timmins et al reported that a small fraction of transfected VP40 can be detected in culture supernatants in association with filamentous particles (Timmins et al., 2001, Virology 283, 1). While we detected VP40 in the supernatants of transfected 293T cells, electron microscopic analysis revealed that the protein was associated with unstructured membrane fragments. In multiple experiments, filamentous particles were only observed when both VP40 and GP were concurrently expressed. These findings imply that the driving force for the assembly and release of EBOV may be the interaction between GP and matrix protein, as suggested previously (Feldman and Klenk, 1996, supra). Ebola VP40 has an N-terminal and a C-terminal domain, the latter being involved in membrane localization (Dessen et al., 2000, EMBO J. 19, 4228). Removal of most of the C-terminal domain induces hexamerization of the protein, the multimeric form believed to be involved in viral assembly (Ruigrok et al., 2000, J. Mol. Biol. 300, 103). While our data show that the majority of VP40 is membrane associated, we were unable to detect VP40 in the rafts when expressed independently (data not shown). Our attempts to detect VP40 in the lipid rafts in the presence of GP was hampered by the efficient release of the proteins in the supernatants resulting in hardly detectable cellular levels of VP40 (FIG. 3). However, given the incorporation of GM1 in the VP40-containing VLPs, it is reasonable to speculate that a transient association of VP40 with lipid rafts takes place in the cells. It is possible that association of VP40 with GP drives VP40 into the rafts. Since a fraction of GP is outside the rafts (FIG. 1), probably in a dynamic exchange with the rafts, this pool of GP might be involved in the initial interaction with VP40. This interaction and subsequent movement to the rafts may, at the same time, induce a conformational change in VP40 resulting in dissociation of the C-terminal domain from the non-raft membrane and thus removing the constraints on the formation of VP40 hexamers required for viral assembly. Detailed studies are underway to test this model. In this regard, the successful generation of VLPs by ectopic expression of viral proteins provides a safe approach for the study of the steps involved in filovirus assembly and budding without the restrictions of biosafety level-4 laboratories.

VLPs could be an excellent vehicle for antigen delivery, thus useful as a vaccination strategy (Johnson and Chiu, 2000, Curr. Opin. Struct. Biol. 10, 229; Wagner et al., 1999, Vaccine 17, 1706). Different types of recombinant HIV-1 virus-like particles have been shown to not only trigger the induction of neutralizing antibodies but also induce HIV-specific CD8[+] CTL responses in preclinical studies (Wagner et al., 1999, supra). Therefore, VLPs are capable of mobilizing different arms of the adaptive immune system. Given the importance of both cellular and humoral immune response for protection against Ebola (Wilson et al., 2000, supra; Wilson and Hart 2001, J. Virol. 75, 2660), filovirus-based VLPs, alone or in combination with DNA vaccination, may represent a good vaccine candidate. Another potential use of VLPs is in the delivery of foreign antigens. Parvovirus-like particles have been engineered to express foreign polypeptides, resulting in the production of large quantities of highly immunogenic peptides, and to induce strong antibody, T helper cell, and CTL responses (Wagner et al., 1999, supra). Given the compartmentalized release of VLPs through rafts, artificial targeting of antigens to lipid rafts by introduction of dual acylation signals may result in their enrichment in filovirus-based VLPs, providing a potential novel strategy for delivery of a variety of antigens.

VLPs are also valuable research tools. Mutational analysis of the proteins involved in filovirus release can be performed using VLP formation as a quick readout. Our VLPs express the envelope glycoprotein in addition to the matrix protein and can therefore be also used for detailed study of the steps involved in the fusion and entry of EBOV and MBGV by circumventing the restrictions of working under biosafety level-4 conditions.

Most enveloped viruses use a specific interaction between their glycoproteins and cell surface receptors to initiate the attachment to the cells and subsequent fusion. Organization of viral receptors in the ordered environment of lipid rafts may facilitate the virus binding through its multimeric glycoprotein, promote lateral assemblies at the plasma membrane required for productive infections, concentrate the necessary cytosolic and cytoskeletal components, and enhance the fusion process by providing energetically favorable conditions. It is intriguing that the HIV receptor CD4 (Xavier et al., 1998, supra), its coreceptor CXCR4 (Manes et al., 2000, supra), as well as molecules favoring HIV infection such as glycosphingolipids (Simons and Ikonen, 1997, supra; Hug et al., 2000, J. Virol. 74, 6377), and CD44 (Viola et al., 1999, supra; Dukes et al., 1995, J. Virol. 69, 4000) all reside in lipid rafts. Our data suggest that filoviruses use lipid rafts as a gateway for the entry into cells. This may relate to the presence of the filovirus receptor(s) in these microdomains. Recently, it has been demonstrated that folate receptor-α can function as a cellular receptor for filoviruses (Chan et al., 2001, Cell 106, 117). Interestingly, folate receptor-α is a GPI-anchored protein shown to reside in the rafts (Nichols et al., 2001, J. Cell Biol. 153, 529). Thus, rafts may be crucial for viral entry by concentrating the receptor for filovirus glycoproteins. Our finding that disruption of lipid rafts can interfere with filovirus entry suggests that the integrity of these compartments or their molecular components may be potential therapeutic targets against Ebola and Marburg infections. Further characterization of the raft composition during host-virus interaction, for instance by proteomic analysis, will help to identify such potential targets.

As described above, we generated enveloped eVLPs and mVLPs by expressing the viral glycoprotein and the matrix protein VP40 in mammalian cells. The eVLPs are completely efficacious in preventing lethal EBOV infection in mice. While mVLPs represent a promising novel subunit vaccine candidate, there are substantial differences in amino acid composition between Marburg and Ebola viruses. Therefore, we undertook the following experiments to test mVLPs for efficacy against deadly MARV infection and to determine the immunogenicity and protective efficacy of mVLPs in a MARV guinea pig model.

EXAMPLE 10

Figure 10:
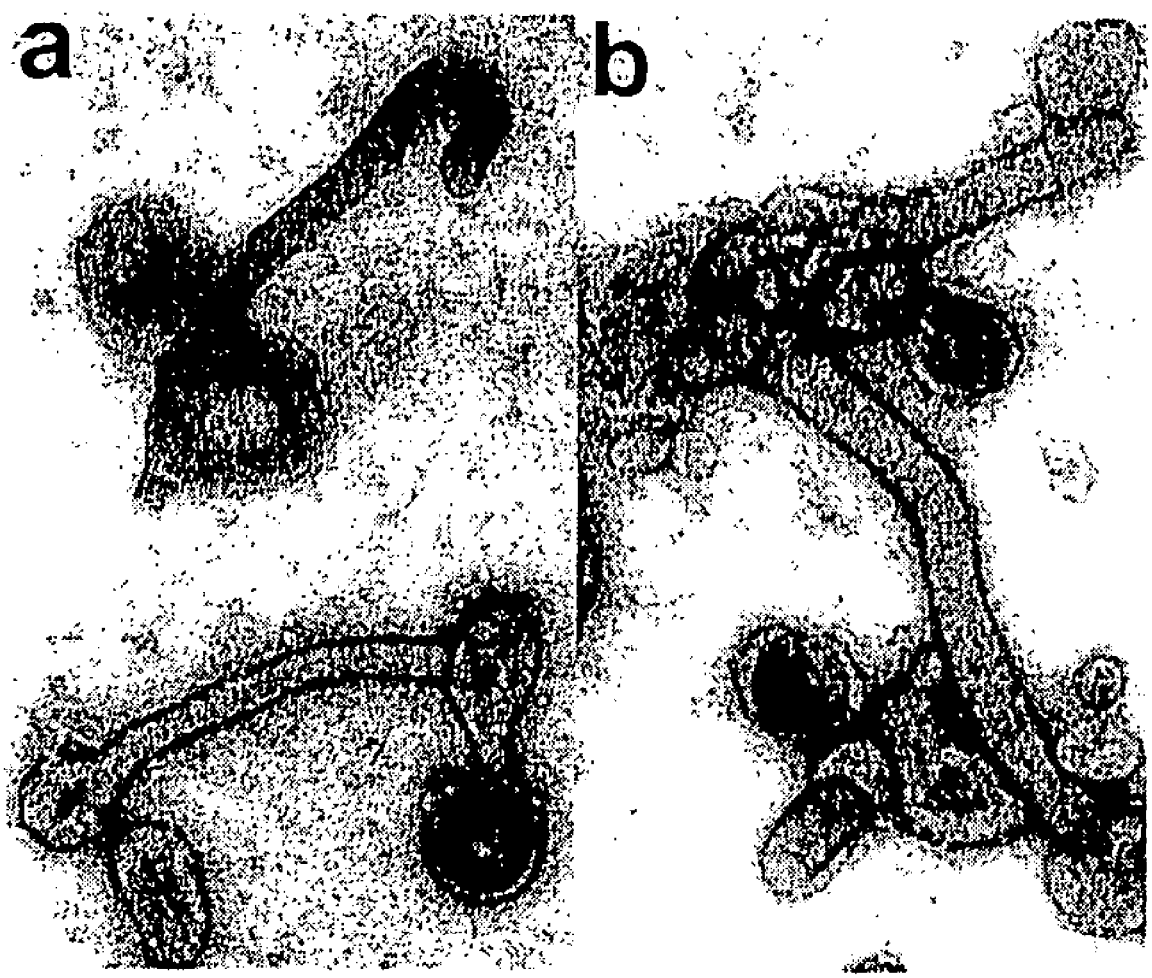
FIGS. 10A and 10B. Marburg virus-like particles (mVLP) are morphologically similar to authentic Marburg virus (MARV) virions. a-b, Electron micrographs of MARV (a) or mVLP (b) at 40,000×. Particles, obtained by ultracentrifugation of the supernatants of MARV GP and VP40 transfected cells or cells infected with MARV virus, were negatively stained with uranyl acetate to reveal the ultrastructure.

VLP vaccination induces humoral responses in guinea pigs. The mVLPs were produced in cells transfected with MARV GP and VP40. After a purification procedure similar to authentic MARV, the mVLPs demonstrated remarkably similar morphology to filovirus virions (FIG. 10). We found both the MARV particles (FIG. 10a) and mVLPs (FIG. 10b) displayed similar heterogeneity, with particles of different lengths and shapes. In general, MARV appeared to be electron dense inside the viral particles, most likely due to the presence of the nucleocapsid proteins and RNA (FIG. 10a). However, some MARV particles appeared hollow, similar to the mVLPs, which contained only the glycoprotein and matrix proteins of MARV. Because the mVLPs and MARV had a similar morphology, but lacked potential virulence factors such as VP35 (Bosio et al., 2003, J. Infect. Dis. 188, 1630-1638), we hypothesized that the genome-free mVLPs would be antigenically similar to MARV and, therefore, useful as a vaccine against lethal MARV infection.

Figure 11:
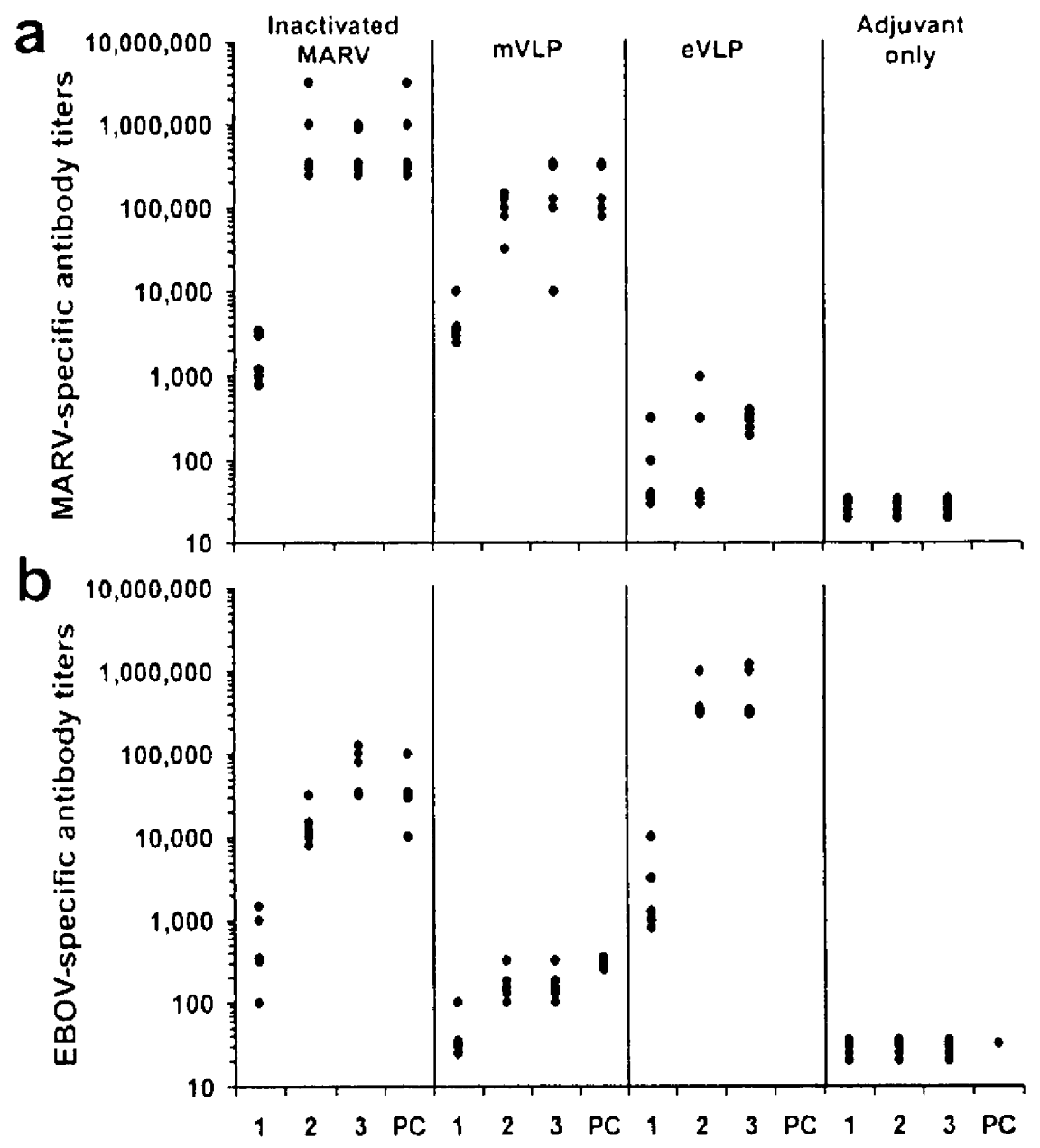

In guinea pigs, strong filovirus-specific antibody responses correlate with vaccine protective efficacy (Hevey et al., 1998, supra; Hevey et al., 2001, Vaccine 20, 586-593; Xu et al., 1998, Nat. Med. 4, 37-42). To assess the immunogenicity of the VLP vaccinations, groups of guinea pigs were vaccinated three times with inactivated MARV, mVLP, eVLP, or diluent and RIBI adjuvant. The guinea pigs were bled 21 days after each vaccination and the levels of MARV- or EBOV-specific antibodies were measured by ELISA (FIG. 11). mVLPs or inactivated MARV quickly elicited serum antibody responses to MARV after a single vaccine (FIG. 11a). Guinea pigs vaccinated three times with inactivated MARV developed MARV-specific antibodies in the range of 331,000-3,310,000. Similarly, guinea pigs vaccinated with mVLP developed high ELISA antibody titers against MARV after three doses (range: 10,000-331,000). Both inactivated MARV and mVLP induced maximal humoral responses to MARV after only two vaccinations (FIG. 11a). Although vaccination with inactivated MARV or mVLPs induced high titers of MARV-specific antibodies, it induced lower levels of cross-reactive antibodies against EBOV (FIG. 11b; endpoint titers ranged from 33,100-100,000 and 100-331 for inactivated MARV and mVLP, respectively). Conversely, guinea pigs vaccinated with eVLP acquired high serum antibody titers against EBOV, ranging from 331,000 to 1,000,000 after three vaccinations (FIG. 11b). However, all of the eVLP-vaccinated guinea pigs had barely detectable levels of anti-MARV antibodies with endpoint titers of 331 (FIG. 11a). Guinea pigs vaccinated with adjuvant alone did not develop MARV- or EBOV-specific antibodies (FIG. 11a-b).

Figure 12:
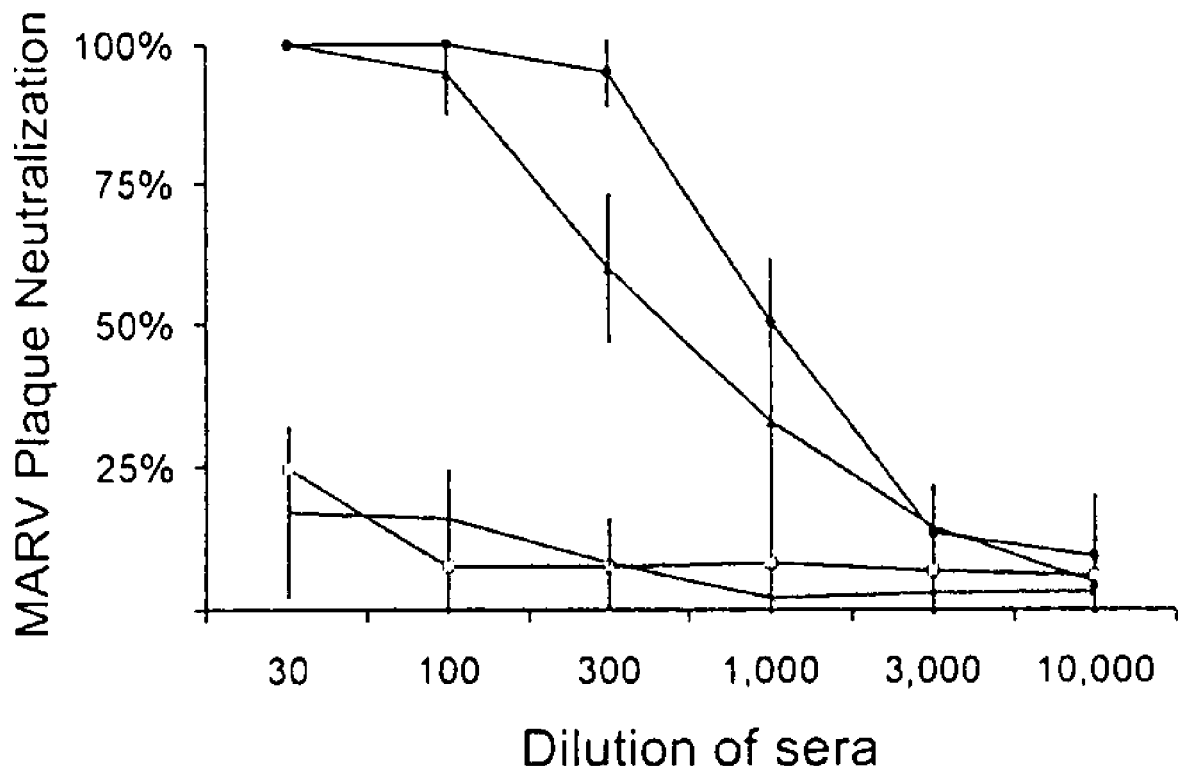

To evaluate the generation of neutralizing antibodies in the sera of the vaccinated guinea pigs, we used the plaque reduction-neutralization test ($PRNT_{80}$). Guinea pigs vaccinated with mVLPs developed neutralizing antibodies with a $PRNT_{80}$ endpoint titer of 1:100 (FIG. 12, n=5). Guinea pigs that received inactivated MARV neutralized 80% or more of the virus up to a dilution of 1:300 (n=5). However, guinea pigs that received eVLP or adjuvant alone were not able to significantly neutralize MARV infection of Vero E6 cells (FIG. 12). Considered together, these data indicate that mVLPs were able to induce high levels of MARV-specific antibodies, as well as neutralizing antibodies against MARV.

EXAMPLE 11

VLP Vaccination Induces $CD4^+$ T Cell Responses

Figure 13:
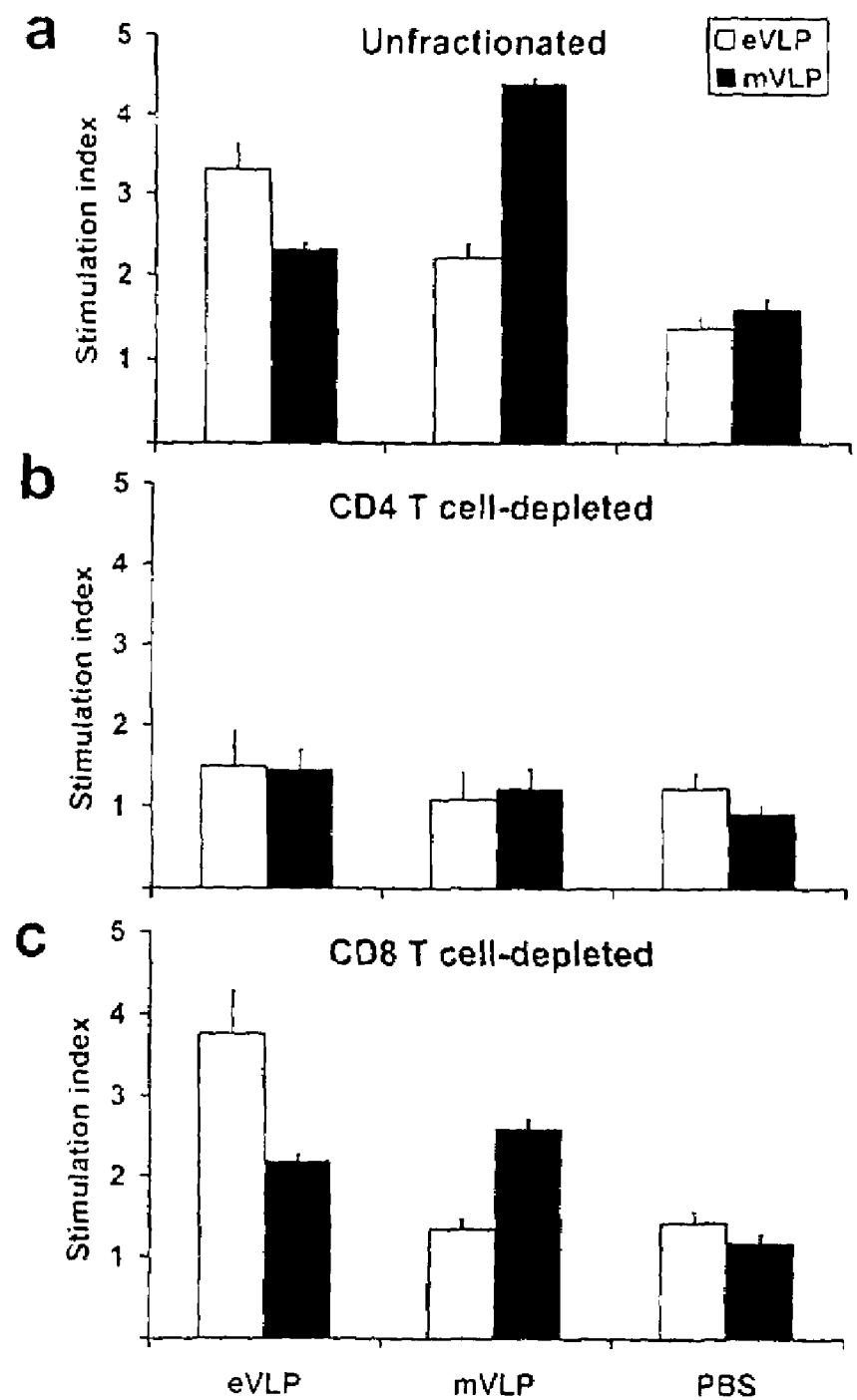
FIGS. 13A, 13B and 13C. VLPs induce recall T cell responses in guinea pigs. Unfractionated (a), CD4+ (b), or CD8+ T cell-depleted (c) splenocytes from guinea pigs vaccinated with mVLP, eVLP, or PBS in RIBI adjuvant were stimulated in vitro with mVLP, eVLP, or media alone for 6 days. During the last 18 hours of culture, $^3$H-thymidine was added to each well and the amount of $^3$H incorporation was assessed. The stimulation index was determined by dividing the $^3$H incorporation in wells stimulated with eVLP (white) or mVLP (black) by the $^3$H incorporation of wells cultured with media alone. The error bars represent the standard deviation of the mean of the stimulation index (n=3).

The generation of cellular immune responses is likely important for protection against pathogenic viruses, such as MARV and EBOV. Previously, Wilson et al. showed that cellular responses to EBOV NP are sufficient for protecting mice against lethal EBOV infection, demonstrating a critical role of T cells in filovirus immunity (Wilson and Hart, 2001, J. Virol. 75, 2660-4). To assess the cellular immune responses generated after VLP injection, splenocytes from vaccinated guinea pigs were re-stimulated in vitro with mVLP or eVLP. Unfractionated T cells from guinea pigs vaccinated with eVLP or mVLP proliferated when re-exposed to the homologous, but not heterologous, antigen (FIG. 13a). To determine whether $CD4^+$ or $CD8^+$ T cells were important for the recall memory responses to VLP vaccination, the splenocytes were depleted of $CD4^+$ or $CD8^+$ T cells and the remaining cells were re-stimulated with VLPs. Depletion of $CD4^+$, but not $CD8^+$, T cells ablated the specific proliferative responses to VLP vaccination, indicating efficient priming of $CD4^+$ T cells by VLP vaccination and suggesting a role for these cells in anti-MARV immune responses (FIG. 13b-c).

Figure 14:
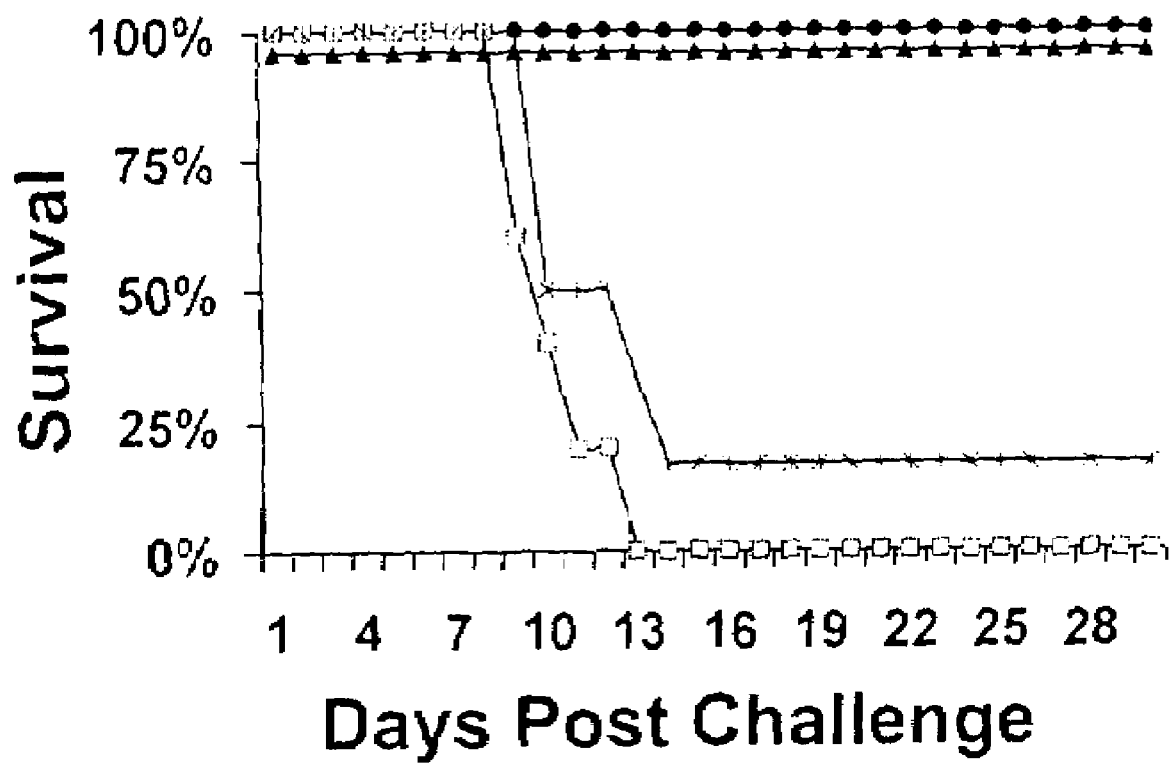
FIG. 14. Marburg VLPs protect guinea pigs against MARV challenge. Strain 13 guinea pigs were vaccinated with 50 μg of inactivated MARV (iMARV) (filled circle), mVLP (filled triangle), or Ebola virus-like particles (eVLP) (open square) in RIBI adjuvant or adjuvant alone (star) three times at three-week intervals. All guinea pigs were challenged with 1000 pfu of guinea pig-adapted MARV-Musoke virus 5 weeks after the last vaccination. Results are plotted as percent survival for each vaccination group (n=5-6 per group).

EXAMPLE 12 mVLP vaccination induces protection against MARV challenge. To determine whether mVLP vaccination could elicit protection from MARV challenge, groups of guinea pigs were vaccinated with three doses of inactivated MARV, mVLP, eVLP, or diluent and RIBI adjuvant and then challenged with 1,000 pfu of guinea pig-adapted MARV-Musoke. Guinea pigs vaccinated with mVLP or inactivated MARV were completely protected from lethal MARV infection (FIG. 14). Additionally, guinea pigs vaccinated with either mVLP or inactivated MARV did not show any visible signs of illness after MARV challenge (data not shown). In concert with lack of clinical symptoms after MARV challenge, the lack of increase in MARV-specific antibody levels after challenge (FIG. 11a) indicates that mVLP vaccination was able to effectively control MARV infection. In contrast, vaccination with eVLPs failed to protect animals from the related filovirus MARV (FIG. 14). eVLP-vaccinated guinea pigs succumbed to lethal MARV infection with kinetics very similar to guinea pigs vaccinated with adjuvant alone (FIG. 14). However, in the eVLP vaccines, MARV challenge appeared to initiate lethality earlier than the control guinea pigs. One guinea pig in the group of six vaccinated with RIBI adjuvant alone did not develop clinical signs of filovirus infection and did not succumb to this lethal challenge dose of MARV (FIG. 14). After challenge with MARV, the lone survivor vaccinated with RIBI adjuvant displayed high MARV-specific antibody levels, indicating it was indeed exposed to MARV (FIG. 11a). Previous studies have shown that the guinea pig-adapted MARV-Musoke is not uniformly lethal, but causes death in ~93% (55/59) of Strain 13 guinea pigs (Hevey et al., 1997, supra; Hevey et al., 1998, supra; Bavari et al., 2002, supra). Therefore, our results are in-line with previous data.

Discussion

So far, we found that Marburg VLPs completely protected guinea pigs from lethal MARV. Vaccination with mVLPs induced strong humoral immune responses including high MARV-specific antibody titers and MARV plaque-neutralizing antibodies. Additionally, mVLP vaccination induced MARV-specific CD4$^+$ T-cell proliferative responses. Similarly, eVLPs induced high titers of EBOV-specific antibodies and T-cell proliferative responses in vaccinated guinea pigs. Not surprisingly considering the limited amino acid homology (~31%) between EBOV and MARV, vaccination with eVLPs did not induce cross-reactive protection from MARV infection (Feldmann and Klenk, 1996, Adv. Virus Res. 47, 1-52). Although the efficacy of the eVLPs has not yet been tested against EBOV infection in guinea pigs, eVLP are highly efficacious in protecting against lethal challenge in a mouse model of EBOV infection (Warfield et al., 2003, Proc. Natl. Acad. Sci. USA 100, 15889-94). Taken together, VLPs are promising vaccine candidates that circumvent the safety, production, or vector immunity concerns associated with other filovirus vaccine candidates.

Figure 20:
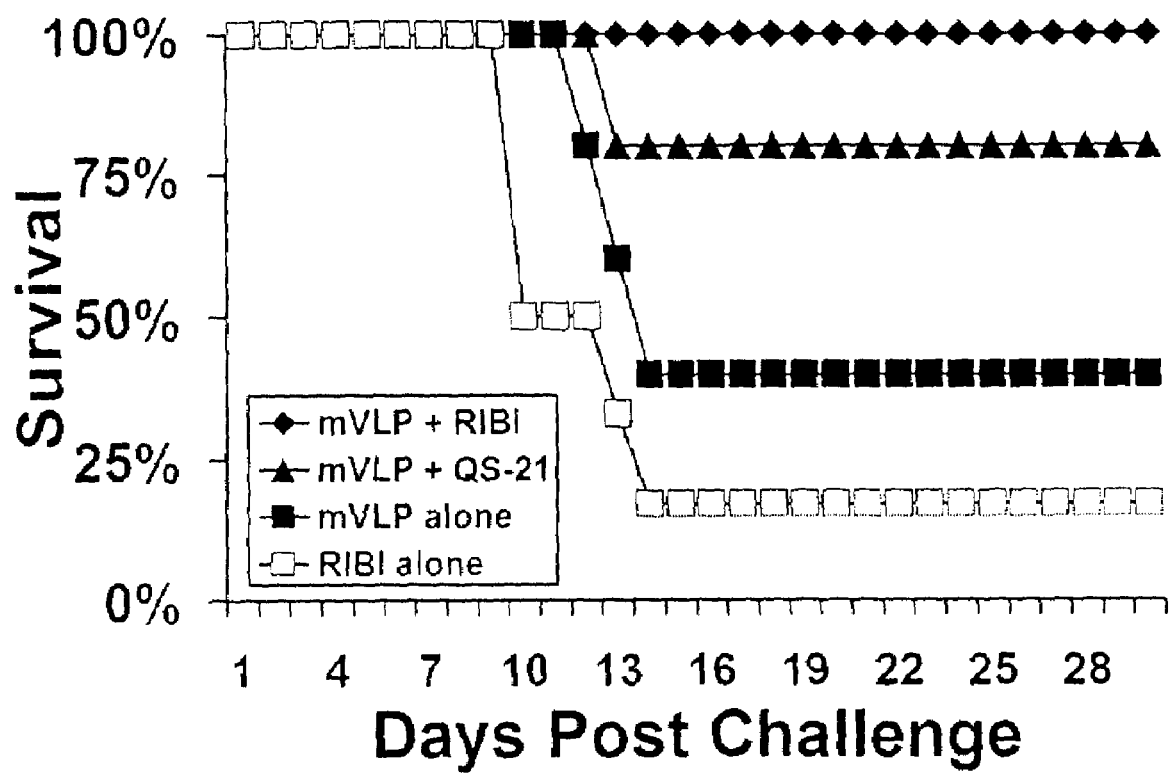
FIG. 20. Vaccination with Marburg VLPs in the presence of adjuvant increases survival of guinea pigs following MARV challenge. Strain 13 guinea pigs were vaccinated with 50 μg of mVLP with RIBI adjuvant (filled diamonds, mVLP with QS-21 adjuvant (filled triangle), mVLP with no adjuvant (filled square) or RIBI adjuvant alone (open square) three times at three-week intervals. All guinea pigs were challenged with 1000 pfu of guinea pig-adapted MARV-Musoke virus 5 weeks after the last vaccination. Results are plotted as percent survival for each vaccination group (n=6 per group).
Figure 21:
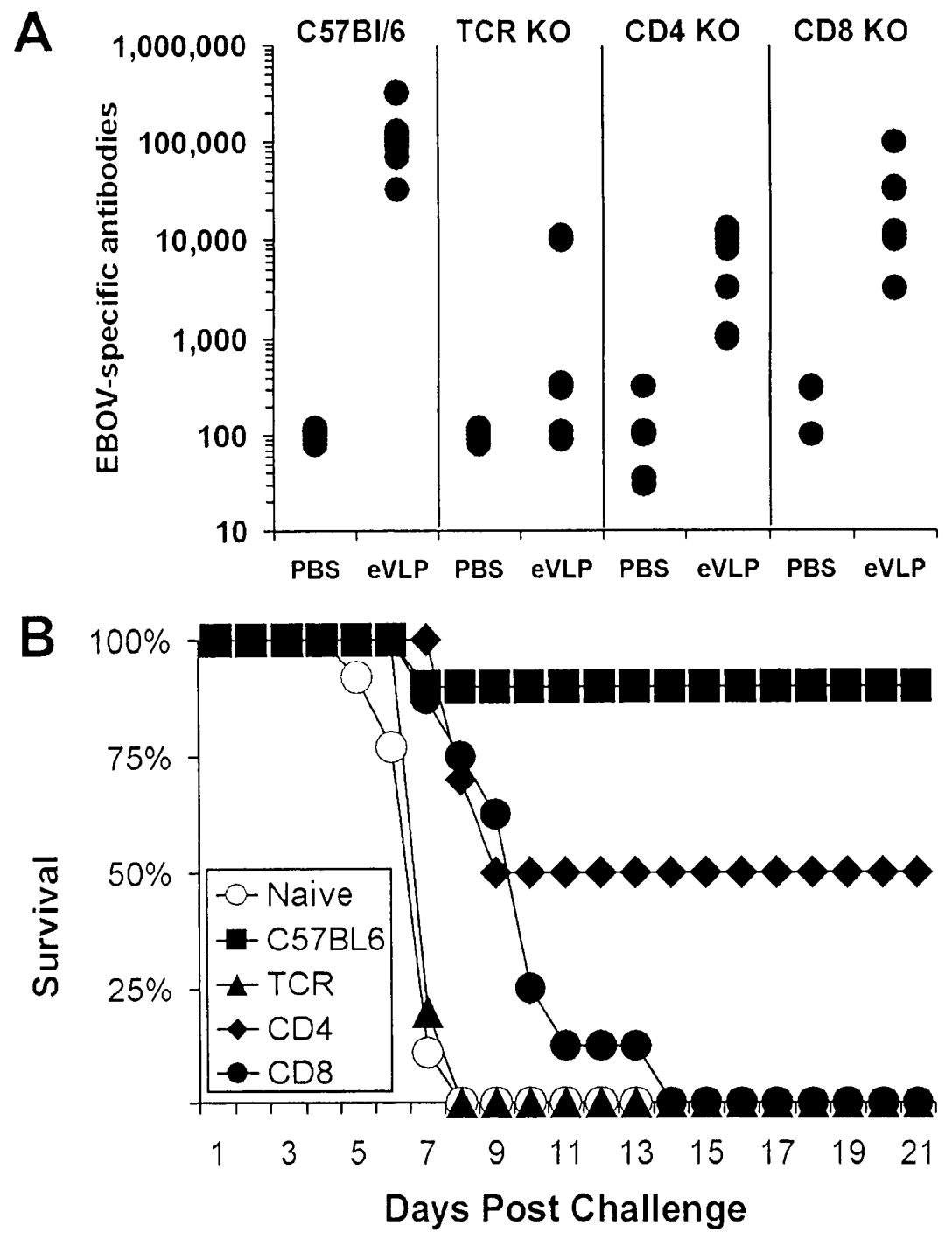

VLP vaccination of guinea pigs induced high levels of total and neutralizing filovirus-specific serum antibodies. The role in protection of VLP-induced MARV-specific antibodies is unclear at this time, although serum from eVLP-vaccinated mice was insufficient to protect against lethal challenge in a mouse model of EBOV infection (Warfield et al., 2003, supra). In contrast, passive transfer of antibodies from MARV-immune guinea pigs can protect naïve animals from MARV challenge in a dose-dependent manner (Hevey et al., 1997, supra). Additionally, MARV-specific monoclonal antibodies can confer partial protection from MARV challenge in guinea pigs (Hevey et al., 2003, Virology 314, 350-357). Together, these data indicate that a certain amount of antibodies with the appropriate specificity, isotype, and avidity are sufficient to protect against MARV infection in guinea pigs (Hevey et al., 1997, supra; Hart, M. K. 2003, International J. Parasitol. 33, 583-595), as they are for EBOV infection in mice (Wilson et al., 2000, Science 287, 1664-1666). In this study we used RIBI adjuvant, however, we have previously shown that the mVLPs are immunogenic in mice in the absence of adjuvant and we are also testing the efficacy of the VLPs alone or in combination with other adjuvants, including the saponin derivative QS-21 (FIG. 20) and mutant *E. coli* heat labile toxin LT(R192G) (FIG. 21). We were encouraged to find that vaccination with inactivated MARV or mVLP induced similar levels of MARV-specific total or plaque-neutralizing antibodies (FIGS. 11 and 12). Additionally, vaccination with inactivated MARV or mVLP elicited levels of MARV-neutralizing antibodies similar to those previously reported after administration of filovirus vaccines or in convalescent animals (Hevey et al., 1997, supra; Hevey et al, 1998, supra; Hevey et al., 2001, supra; Xu et al., 1998, supra; Hart, M. K., 2003, supra).

The role of T-cell responses in protection against filovirus infection is also not well understood, but it is generally accepted that cellular immune responses are required to achieve complete protection against filovirus infection. Splenocytes from guinea pigs vaccinated with mVLPs specifically proliferated in culture in response to mVLP, but showed no proliferative response to eVLPs, while the opposite was true for guinea pigs vaccinated with eVLPs (FIG. 14). This proliferative response to VLPs required CD4$^+$ T cells, since depletion of CD4$^+$, but not CD8$^+$, cells ablated T cell stimulation. Similar to our findings, guinea pigs vaccinated with a prime-boost strategy of DNA and adenovirus vaccines encoding EBOV GP and NP, depletion of CD4$^+$, but not CD8$^+$, T cells reduced the recall responses to EBOV GP (Sullivan et al., 2000, Nature 408, 605-609). While examining the role of specific cell types in guinea pigs in vivo is very difficult due to a lack of characterization and availability of antigens, depletion of cell types of interest, adoptive transfers, and knockout mice can be used to dissect the importance of specific immune components for protection against filovirus infection. Unfortunately, no mouse model is currently available for MARV. The mouse model of EBOV has been exploited to determine that successfully vaccinating mice with liposome-encapsulated irradiated EBOV requires CD4$^+$ T cells. In contrast, using knockout mice, we found that CD8$^+$ T cells are required for eVLP-mediated protection from EBOV infection (FIG. 21).

Cytotoxic T lymphocytes (CTLs) are proposed to be critical for protection against EBOV (Wilson and Hart, 2001, supra; Hart, M. K., 2003, supra). CD8$^+$ T cells did not contribute to the recall response to VLPs in our culture system. It is well documented that memory CD8$^+$ T cells respond within hours of stimulation, as opposed to CD4$^+$ T-cell recall responses, which can take days to regenerate (Price et al., 1999, Immunol. Today 20, 212-216). Therefore, an inherent problem of antigen recall assays is their bias towards examining CD4$^+$ T cell responses and we think it is likely the timing of this particular assay may have masked any CD8$^+$ T cell response toward the VLPs. Due to a lack of characterization of the guinea pig immune system, it is not currently possible to characterize the epitopes recognized by CD8$^+$ T cells after VLP vaccination. For EBOV, several vaccine strategies including liposomes encapsulating inactivated EBOV, DNA prime/adenovirus boost, and alphavirus-replicon vaccines induce CTL responses against EBOV-specific epitopes of GP and/or NP in mice (Rao et al., 2002, J. Virol. 76; Xu et al., 1998, supra; Wilson and Hart, 2001, supra; Vanderzanden et al., 1998, Virolog 246, 134-144). Evidence for the importance of these CTL responses was demonstrated when adoptive transfer of nucleoprotein-specific CTLs, but not antibody, conferred protection against lethal EBOV infection in naïve mice (Wilson and Hart, 2001, supra). CD4$^+$ and CD8$^+$ T cell responses are generated in mice vaccinated with eVLP (Warfield et al., 2003, supra). For EBOV, there appears to be an absolute requirement for CD8$^+$ T cells to achieve protection from lethal EBOV infection (FIG. 21). While it is unclear at this time whether CD4$^+$ or CD8$^+$ T cells are required for mVLP-induced immunity, it is likely that the generation of both effective T cell and humoral responses to filovirus antigens, especially glycoprotein, are critical.

This is the first report that eVLP-vaccination of guinea pigs efficiently induces humoral and cellular immune responses to EBOV and eVLP, respectively. Our current study shows that the cross-reactive immune responses induced by eVLP are not sufficient to protect against MARV infection. In fact, vaccination with eVLP tended to decrease the survival time following MARV challenge, when compared to control guinea pigs (FIG. 14). Other data indicate that in both rodents and nonhuman primates, ineffectual immune responses following vaccination with inactivated virus or other filovirus antigens can cause accelerated disease progression and an "early-death" phenomenon, when compared to naïve animals (Hevey et al., 1998, supra; Ignatyev et al., 1996, J. Biotechnol. 44, 111-118; Warfield et al., 2003, supra; Ignatyev, G. M., 1999, Curr. Top. Microbiol. Immunol. 235, 205-217; and data not shown). Several mechanisms could be responsible an immune-mediated exacerbation of disease in unprotected animals, including mechanisms involving antibodies (Takada et al., 2001, J. Virol. 75, 2324-2330; Takada and Kawaoka, 2003, Rev. Med. Virol. 13, 387-398). While the significance of this observation is not clear at this time, it could be important for consideration in future vaccine development and points to the importance of developing a pan-filovirus vaccine that broadly protects against all subtypes of both EBOV and MARV. To this end, VLPs provide an excellent system for generating broad-spectrum vaccines, since glycoprotein molecules from different filovirus strains can be efficiently incorporated into these particles (Swenson, 2005, Vaccine, 23, 3033-42).

In summary, we demonstrated that MARV and EBOV VLPs are highly immunogenic in guinea pigs, inducing both humoral and cellular responses against these filoviruses. Importantly, mVLPs completely protected animals against a high-dose parenteral MARV challenge. Marburg VLPs were highly efficacious with multiple advantages not offered by other candidate vaccines such as the safety of a subunit vaccine, no prior immunity to or interference by a vector, and presentation of the critical viral proteins glycoprotein and VP40 in a native form. This report extends our previous work, which demonstrated protective immunity in eVLP-vaccinated mice and provides further evidence to support future studies to evaluate the efficacy of VLPs for both MARV and EBOV in nonhuman primates.

These studies indicated that vaccine strategies that are protective against a homologous filovirus challenge are not efficacious against a heterologous challenge. Therefore, it was important to develop a pan-filovirus vaccine that can protect against multiple and diverse filovirus infections. The following studies were aimed at identifying a vaccine candidate that could provide resistance against diverse members of the family Filoviridae, using EBOV Zaire and MARV-Musoke as models.

EXAMPLE 13

Generation of Hybrid Filovirus-Like Particles

Previous observations determined that GP and VP40 are sufficient, in both EBOV and MARV, to produce VLPs with morphology similar to that of authentic virus (Rao et al., 2002, supra; Sullivan et al., 2003, supra). As a first approach to generating a pan-filovirus vaccine, we sought to generate hybrid VLPs harboring proteins of different filoviruses. EBOV and MARV are members of the same family and cause similar diseases, but are genetically distinct, with only ~30% homology at the amino acid level (Bavari et al., 2002, supra). The structural requirements for filovirus assembly are poorly understood (Rao et al., 2002, supra; Vanderzanden, 1998, supra) and it was not known whether just these two proteins from different filoviruses would cooperate to form VLPs. EBOV GP has been successfully incorporated into pseudotyped murine leukemia virus particles, indicating its promiscuity (Warfield et al., 2003, supra). More recently, GP molecules from distinct filovirus subtypes and strains were incorporated into virus-like particles containing all seven EBOV structural proteins (Watanabe, 2004, J. Virol, 78, 999-105).

Figure 15:
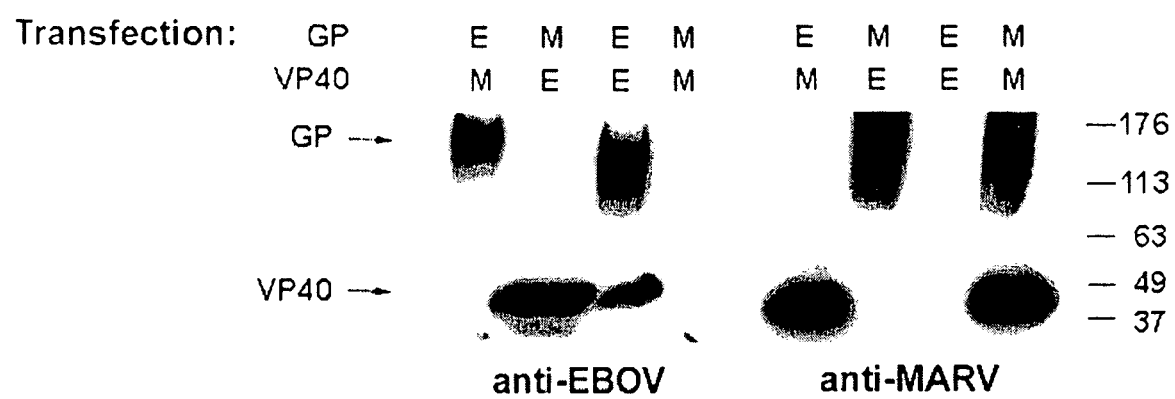
FIG. 15. Detection of Ebola and Marburg virus GP and VP40 by western blot analysis. 293T cells were transfected with combinations of Ebola and Marburg virus (EBOV and MARV, respectively) GP and VP40, as indicated. The viral origin of the GP and VP40 proteins are specified by (E) for EBOV or (M) for MARV. The virus-like particles (VLPs) from supernatants of the transfected cells were purified on a 20-60% continuous sucrose gradient, successive gradient fractions were collected, and then analyzed by western blotting. A representative fraction containing the indicated VLPs is shown here. The presence of wild-type or hybrid VLPs were determined using EBOV- or MARV-specific GP and VP40 monoclonal antibodies.

In order to assess the ability of GP and VP40 from EBOV and MARV to assemble and form hybrid VLPs, 293T cells were transfected with cDNAs encoding MARV GP and EBOV VP40, or alternatively the cells were transfected with EBOV GP and MARV VP40. By western blot, EBOV GP-specific anti-serum recognized the GP incorporated into the VLPs produced from cells transfected with EBOV GP and EBOV or MARV VP40, while EBOV VP40 was found in preparations from cells transfected with either EBOV or MARV GP and EBOV VP40 (FIG. 15). MARV GP-specific anti-serum detected GP in preparations containing MARV GP and MARV VP40 or MARV GP and EBOV VP40 (FIG. 15). MARV VP40 was detected in preparations from cells transfected with MARV GP and MARV VP40, or EBOV GP and MARV VP40 (FIG. 15).

Figure 16:
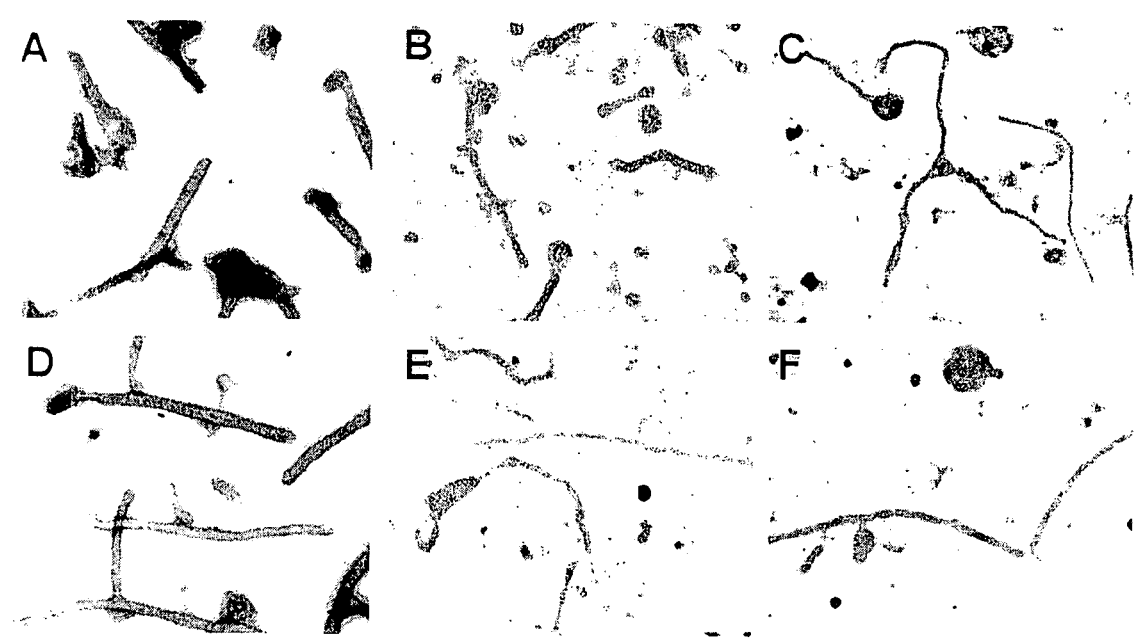
FIGS. 16A, 16B, 16C, 16D, 16E and 16F. Hybrid VLPs are morphologically similar to authentic filoviruses and wild-type VLPs. VLPs, purified from the supernatants of 293T cells transfected with combinations of EBOV and MARV GP and VP40, were negatively stained with uranyl acetate to reveal the ultrastructure. Electron micrographs of (a) authentic EBOV, (b) Ebola virus-like particles (eVLP), (c) VLPs containing EBOV GP and MARV VP40 (e/m-VLP), (d) authentic MARV, (e) Marburg virus-like particles (mVLP), or (f) VLPs containing MARV GP and EBOV VP40 (m/e-VLP) at 40,000×.
Figure 17:
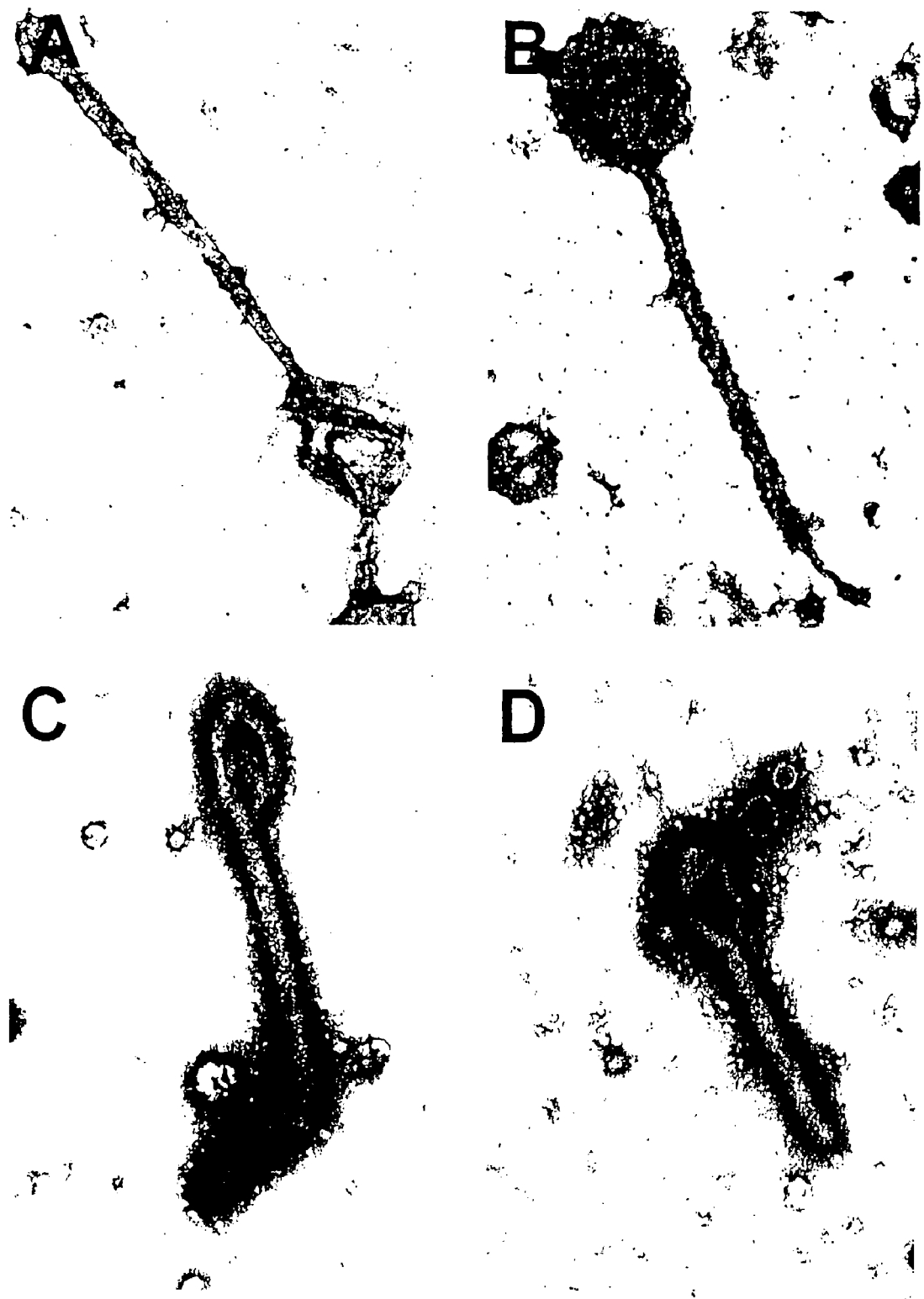
FIGS. 17A, 17B, 17C, and 17D. Hybrid virus-like particles (VLPs) are antigenically similar to wild-type VLPs. Immunoelectron microscopy was performed to demonstrate the specificity of the GP on the (a) eVLPs, (b) e/m-VLPs, (c) mVLPs, or (d) m/e-VLPs at 40,000×. To show that the VLPs contained the GP molecules of the correct specificity, the VLPs were labeled with EBOV—(a-b) or MARV-specific (c-d) monoclonal antibodies against GP followed by immunogold rabbit anti-mouse antibody and examined by electron microscopy.

To determine if the fractions isolated from the sucrose gradients contained filamentous particles, we used electron microscopy. As shown in FIG. 16, hybrid VLPs displayed morphology similar to the wild-type VLPs containing the homologous proteins or to the authentic filoviruses. The hybrid VLPs were designated e/m-VLPs (containing Ebola GP and Marburg VP40) and m/e-VLPs (containing Marburg GP and Ebola VP40). Using immunogold staining of the VLPs with EBOV GP antibodies, we confirmed the presence of EBOV GP spikes on the eVLP and e/m-VLPs (FIG. 17a-b), but not the mVLPs or m/e-VLPs (data not shown). Similarly, mVLP and m/e-VLPs displayed gold staining after incubation with MARV GP antibodies (FIG. 17c-d), but eVLPs and e/m-VLPs did not react with the MARV GP antibodies (data not shown). Taken together, these data show that heterologous EBOV and MARV proteins can cooperate to form hybrid VLPs.

EXAMPLE 14

Evaluation of Hybrid VLPs as a Potential Pan-Filovirus Vaccine

Having the hybrid VLPs in hand, we sought to examine the ability of these structures, as vaccines, to generate protective immunity against both EBOV and MARV in guinea pigs. In addition, the hybrid VLPs gave us a powerful tool to examine the contribution of GP and VP40 in protective immunity against filoviruses. Guinea pigs were vaccinated once with wild-type eVLPs, mVLPs, hybrid e/m-VLPs, or m/e-VLPs in RIBI adjuvant and their serum antibody levels against EBOV and MARV were measured by ELISA immediately prior to challenge (Table 1). Guinea pigs vaccinated with wild-type eVLP or e/m-VLPs generated high serum antibody titers against EBOV [geometric mean titer (GMT): 8,075 and 19,509, respectively], but not MARV (GMT: 53 and 30, respectively). Conversely, mVLP and m/e-VLP vaccination resulted in high titers against MARV (GMT: 19,595 and 13,856, respectively), but not EBOV (GMT: 47 and 54, respectively). Vaccination with EBOV GP in the form of eVLP or e/m-VLP resulted in induction of neutralizing antibodies against EBOV, but not MARV (Table 1). In contrast, guinea pigs vaccinated with mVLP or m/e-VLP did not generate significant neutralizing antibody titers against either MARV or EBOV after one dose of vaccine (Table 1). Control guinea pigs, vaccinated with RIBI adjuvant alone, did not display EBOV- or MARV-specific antibodies (Table 1).

Because the VLP-vaccinated animals generated strong antibody responses after one vaccination and, in guinea pigs, protective efficacy of filovirus vaccines correlate positively, although imperfectly, with filovirus-specific antibody responses (Geisbert et al, 2002, Emerg. Infect. Dis. 8,503-507; Hevey et al., 1997, supra; Warfield et al., 2004, supra), the guinea pigs were challenged 28 days after a single VLP vaccination with ~1,000 pfu of guinea pig-adapted EBOV or MARV. Guinea pigs vaccinated with VLPs containing the homologous GP were protected ($\geq 90\%$) from lethal filovirus challenge (Table 1). A single vaccination with eVLP or e/m-VLP conferred significant protection against EBOV infection ($\rho=0.0002$ or 0.0014, respectively, when compared to RIBI-vaccinated animals) and mVLP or m/e-VLP completely protected MARV-challenged guinea pigs

TABLE 1

Homologous, but not heterologous GP, confers protection from Ebola virus (EBOV) and Marburg virus (MARV) in the context of virus-like particles (VLPs) containing EBOV or MARV glycoprotein (GP) or viral protein (VP)40

| Vaccine[a] | Geometric Mean Titer[b] | | PRNT$_{80}$[c] | | Viremia (log10 pfu/ml)[d] | | Survival[e] | | Mean Time to Death (days) | |
|---|---|---|---|---|---|---|---|---|---|---|
| | EBOV | MARV | EBOV | MARV | EBOV | MARV | EBOV | MARV | EBOV | MARV |
| eVLP | 8,075 | 53 | 448 | <10 | <1.7 | 5.61 | 10/10 | 2/8 | — | 12.8 |
| mVLP | 47 | 19,595 | <10 | 16 | 5.73 | <1.7 | 0/10 | 10/10 | 10.3 | — |
| e/mVLP | 19,509 | 30 | 75.2 | <10 | <1.7 | 5.82 | 9/10 | 1/9 | —[f] | 12 |
| m/eVLP | 54 | 13,856 | <10 | 14 | 5.98 | <1.7 | 0/10 | 10/10 | 9 | — |
| RIBI adjuvant | 29 | 59 | <10 | <10 | 6.08 | 5.82 | 0/10 | 5/19 | 9.3 | 10.8 |
| naïve | 33 | 43 | ND | ND | 6.03 | 5.83 | 0/6 | 1/6 | 10 | 9.2 |

[a]Guinea pigs were injected with one dose of the indicated vaccine and 28 days later were challenged with 1000 pfu of guinea pig-adapted EBOV or MARV virus The indicated vaccines contained 100 ug of VLPs comprised of EBOV or MARV GP and VP40 (eVLP and mVLP, respectively) or EBOV GP and MARV VP40 (e/mVLP) or MARV GP and EBOV VP40 (m/eVLP). The VLP vaccines were given in 200 uL of RIBI adjuvant. Control groups received 200 ul of RIBI adjuvant or were completely naïve.
[b]Geometric mean titer (n = 6–10) of EBOV- or MARV-specific antibodies, as measured by ELISA, from serum samples collected 28 days post vaccination
[c]Mean plaque reduction/neutralization titer (PRNT, >80% reduction) from serum samples collected 28 days post vaccination, where the dilutions began at 1:10
[d]As measured by plaque assay from serum samples collected 7 days following challenge, with a limit of detection of ~50 pfu/ml
[e]Indicates the number of survivors/total number of guinea pigs at 28 days post challenge
[f]A single vaccinee died on day 13 following challenge

TABLE 2

MARV-Musoke VLPs protect against heterologous challenge with MARV-Ravn and -Ci67

| Vaccine[a] | Mean Antibody Titers[b] | | | Survival following challenge[c] | | |
|---|---|---|---|---|---|---|
| | Musoke | Ravn | Ci67 | Musoke | Ravn | Ci67 |
| MARV-Musoke VLPs | 316,228 | 31,628 | 100,000 | 100% | 100% | 100% |
| Inactivated MARV | 1,000,000 | 100,000 | 100,000 | 100% | 100% | 100% |
| Adjuvant only | <32 | <32 | <32 | <32 | <32 | <32 |

[a]Guinea pigs were vaccinated on day 0 with 100 ug of MARV-Musoke antigen with RIBI adjuvant
[b]Circulating antibody titers in the vaccinated guinea pigs (n = 27/group) were determined using ELISA using antigen from three different MARV strains (Musoke, Ravn, or Ci67)
[c]Guinea pigs (n = 7/group) were challenged 28 days after challenge with 1000 pfu of guinea pig-adapted MARV virus (Musoke, Ravn, or Ci67) and the results are presented as the percent survival 28 days post challenge ($\rho$=0.0026, for both, when each was compared to RIBI-vaccinated animals). However, vaccines containing only heterologous proteins or homologous VP40 were not able to protect against lethal filovirus challenge. For instance, mVLP or m/e-VLP was entirely ineffective in preventing lethal EBOV infection (Table 1). Additionally, eVLP and e/m-VLP only provided 25% and 11% protection, respectively, against a MARV challenge (Table 1). The failure of the hybrid vaccines to protect against EBOV and MARV challenge was not due to challenge following administration of a single dose, as administering three doses of hybrid VLPs prior to virus challenge was not able to protect against both lethal infections (data not shown). Only 14 of 19 RIBI adjuvant-vaccinated guinea pigs (77%) succumbed to challenge (Table 1). We were concerned that the guinea pig-adapted MARV-Musoke was not uniformly lethal, but previous studies caused death in only 60 of 65 (92%) of Strain 13 guinea pigs (Hart, M. K. 2003, supra; Hevey et al., 1997, supra; Rao et al., 2000, supra; Reimenschneider et al., 2003, Vaccine 21, 4071-80). The death rate in the guinea pigs vaccinated with RIBI adjuvant was slightly lower than we expected, despite the fact that our actual challenge doses (intended 1000 pfu) ranged between 452 and 2,672 pfu. Naïve guinea pigs were challenged to account for the effect of the RIBI adjuvant, which was given 28 days prior to challenge, and 5 of 6 MARV-infected guinea pigs died (83%, Table 1). When taken with the previous data, this indicates that the MARV-Musoke adapted to guinea pigs is not uniformly lethal in the Strain 13 guinea pigs.

To determine if VLP vaccination induced sterile immunity, the levels of circulating virus were assessed 7 days after challenge. In correlation with the ability to confer protection against lethal filovirus infection, vaccination with VLPs containing homologous GP resulted in no detectable viremia on day 7 (Table 1). However, control guinea pigs or guinea pigs vaccinated with only heterologous proteins or homologous VP40 had high levels of circulating EBOV (range: 544,000-1,200,000 pfu/ml) or MARV (range: 409,000-681,000 pfu/ml) at 7 days post challenge. These data indicated that GP is the critical protective antigen in the VLPs, and that VP40 may only be required to obtain the filamentous VLP structures, supporting previous observations about GP (Geisbert et al., 2002, supra; Hevey et al., 1997, supra).

EXAMPLE 15

Pan-Filovirus VLP Vaccine Protects against Both MARV and EBOV Lethal Challenge.

Figure 18:
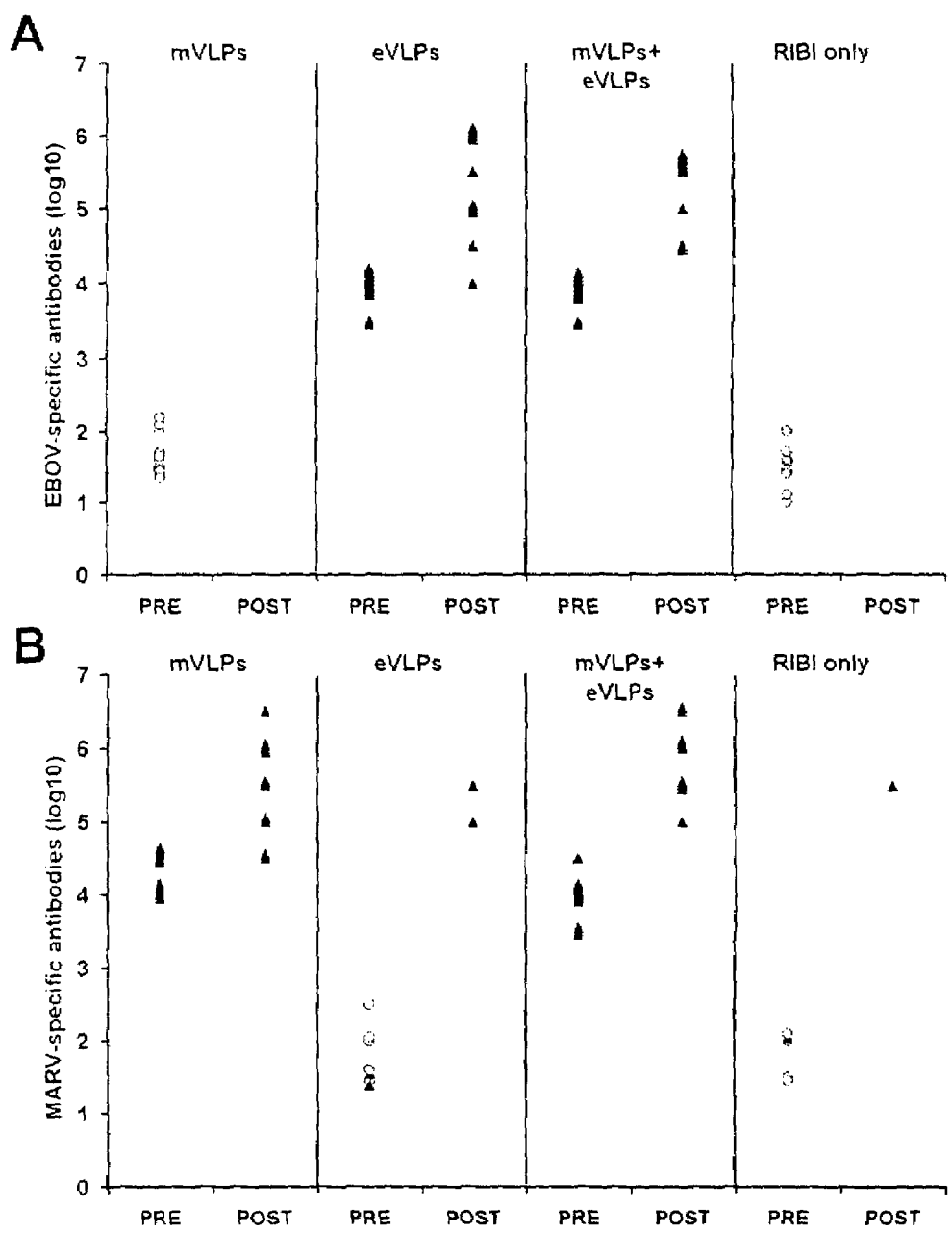
FIGS. 18A and 18B. Serum antibody responses to EBOV and MARV after VLP vaccination. Strain 13 guinea pigs were vaccinated once with eVLPs, mVLPs, or an equal mixture of eVLPs and mVLPs in RIBI adjuvant. Control guinea pigs were vaccinated with RIBI adjuvant alone. Serum samples from the guinea pigs were obtained immediately before (PRE) or 28 days post-challenge (POST). Total serum (a) anti-EBOV or (b) MARV antibodies were measured by ELISA. Antibody titers were measured in serum from individual guinea pigs and the results are graphed as the individual endpoint titers for each guinea pig in each group (n=5-10 per group). Guinea pigs that survived lethal challenge with (a) EBOV or (b) MARV are indicated by the closed triangles and those that died are depicted by open circles.

Because broad protection against both EBOV and MARV was not provided by the hybrid e/m- and m/e-VLPs, we sought to determine whether a mixture of eVLP and mVLP administered at the same time would protect guinea pigs against lethal challenge with both EBOV and MARV. To this end, animals were vaccinated once with a vaccine composed of an equal mixture of eVLPs and mVLPs and challenged with a lethal dose (~1,000 pfu) of either EBOV or MARV. Before challenge, the guinea pigs vaccinated with eVLP and mVLP elicited high antibody titers against both EBOV and MARV (FIG. 18). The titers generated to the homologous antigen were similar to those developed by animals vaccinated with eVLP or mVLP alone, indicating that vaccinating with both antigens at the same time did not interfere with their ability to initiate humoral responses to the individual antigens (FIG. 18).

Figure 19:
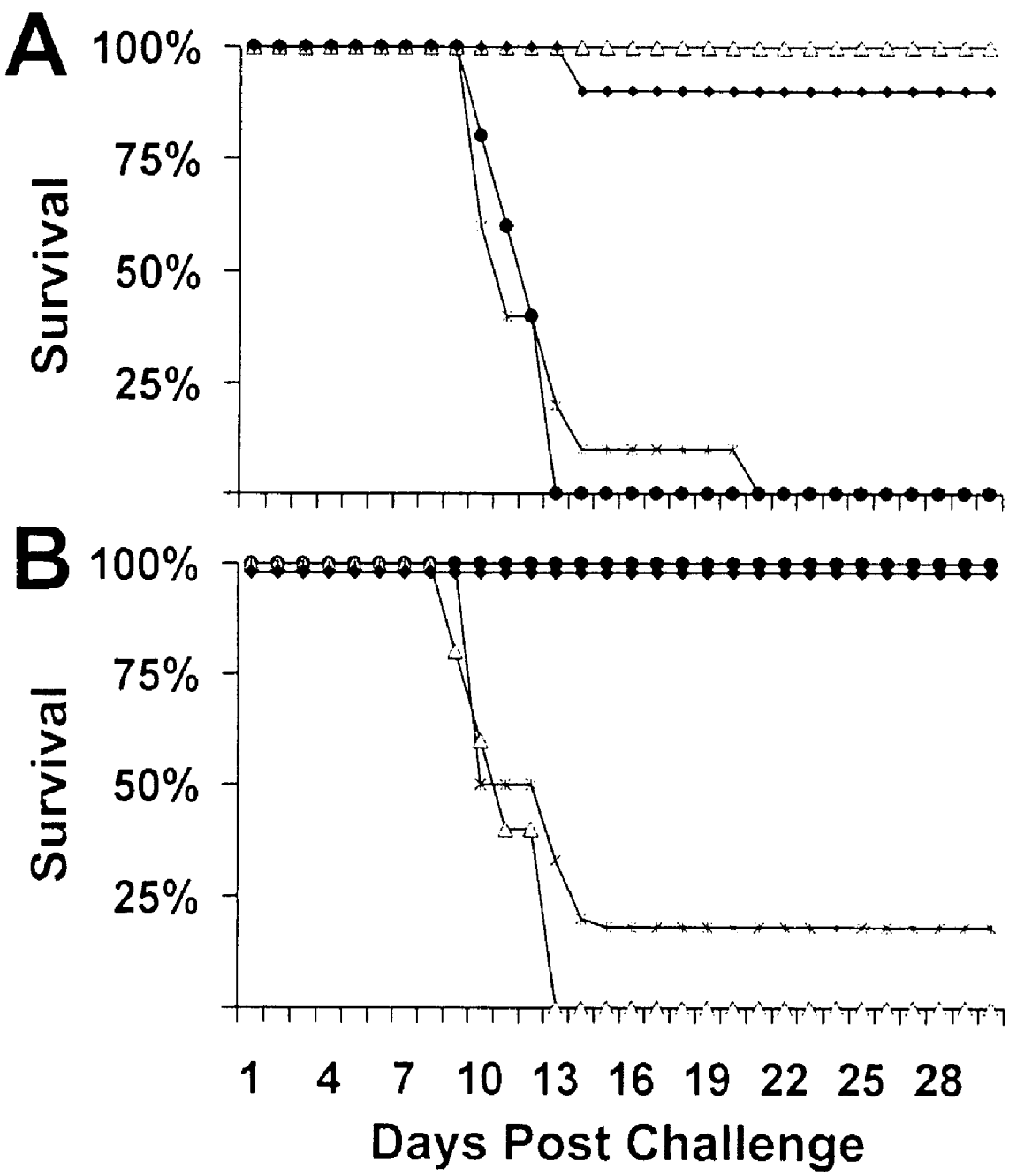
FIGS. 19A and 19B. Pan-filovirus VLP vaccine protects guinea pigs against both EBOV and MARV challenge. Strain 13 guinea pigs were vaccinated once with 100 μg of eVLP (open triangle), mVLP (filled circle), or an equal mixture of both eVLP and mVLP (filled diamond), in RIBI adjuvant or RIBI adjuvant alone (star). The vaccinated guinea pigs were challenged with 1000 pfu of guinea pig-adapted EBOV-Zaire (a) or MARV-Musoke (b) virus 28 days post-vaccination. Results are plotted on Kaplan-Meier survival curves and presented as the percent survival for each vaccination group (n=5-10 per group).

As shown in FIG. 19, vaccination with the pan-filovirus vaccine comprised of a mixture of eVLP and mVLP conferred high levels of protection against a lethal challenge of EBOV (9 survivors out of 10 vaccinated guinea pigs) or MARV (10 survivors in 10 vaccinated guinea pigs), which was significant when compared to animals vaccinated with adjuvant alone (p=0.0014 or 0.0026, respectively). The robust protection observed following vaccination with the mixture of eVLP and mVLP was similar to the protection observed in the groups of animals vaccinated with eVLP or mVLP alone and challenged with the homologous virus. Vaccination with adjuvant alone or the heterologous VLPs resulted in poor survival after lethal filovirus challenge (FIG. 19). All the VLP-vaccinated guinea pigs that survived lethal challenge did not have detectable circulating virus 7 days after challenge, unlike the guinea pigs that succumbed to disease (data not shown). Guinea pigs that survived challenge, including naïve animals, demonstrated an increase in their antibody titers indicating that they were exposed to the virus (FIG. 18).

Discussion

We sought to develop a pan-filovirus vaccine using VLPs that could protect against multiple filovirus infections. As a first approach toward generation of pan-filovirus vaccines, we produced hybrid VLPs containing heterologous GP and VP40. These hybrid VLPs were useful in determining that the homologous GP, but not VP40, was required and sufficient for protection against lethal challenge with homologous virus in guinea pigs. However, the hybrid VLPs did not provide broad protection against both EBOV and MARV, so we developed a pan-filovirus vaccine comprised of a mixture of eVLP and mVLP. This pan-filovirus vaccine induced strong humoral immune responses, similar to vaccination with eVLP or mVLP alone. Encouragingly, the multivalent VLP vaccine provided almost complete protection (>90%) against lethal challenge with either EBOV or MARV.

While MARV and EBOV are both members of the family Filoviridae, they have been classified in a different genera and exhibit very little similarity at the amino acid level, with the GP and VP40 proteins having less than 30% identity between EBOV-Zaire and MARV-Musoke strains (Bavari et al., 2002, supra). The incorporation of MARV GP has previously been shown onto 'wild-type' VLPs containing all seven structural EBOV proteins (Warfield et al., 2004, supra). However, it was unknown whether GP and VP40 alone from the heterologous EBOV and MARV would associate within a cell, bud from the lipid rafts, and form functional VLPs without the presence of the other structural proteins. Here, we demonstrate that GP and VP40 from the genetically distinct viruses, EBOV-Zaire and MARV-Musoke, were able to co-associate and form VLPs. Furthermore, these hybrid VLPs exhibited morphological characteristics similar to live EBOV and MARV, as well as to Ebola and Marburg VLPs. The elements required for filovirus assembly are only beginning to be unraveled; however, we found that the generation of VLPs provides a useful tool to safely and easily dissect the cellular and viral requirements for assembly (Rao et al., 2002, supra; Vanderzanden et al., 1998, supra). Because VP40 and GP naturally target the cellular lipid rafts (Rao et al., 2002, supra; Wilson et al., 2001, Virology 286, 384-90), it is unknown at this time whether these molecules specifically interact to form VLPs, or whether it is a consequence of their localization to the same compartments within the cell. However, these data suggest that despite the limited homology, both viruses use similar mechanisms for assembly and release of filamentous structures.

Our finding that GP is sufficient and required for homologous protection is supported by previous studies showing that an immune response to GP is adequate for protection. Administration of MARV GP presented as a VRP or DNA vaccine successfully protected cynomolgus macaques from lethal MARV challenge (100% or 66%, respectively) (Geisbert et al., 2002, supra; Hevey et al., 1997, supra; Martini and Siegert, 1971, Marburg Virus Disease. Springer Verlag, Berlin). Similarly, EBOV GP presented in a prime-boost strategy using DNA and adenovirus vaccines, protected monkeys from EBOV infection (Panchal et al., 2003, Proc. Natl. Acad. Sci. USA 100, 15936-41). A VRP vaccine expressing GP protected mice and guinea pigs from lethal EBOV infection, but it was not sufficient to protect cynomolgus macaques from lethal EBOV infection (Feldmann et al., 1993, Arch. Virol. Suppl. 7, 81-100; Hevey et al., 1998, supra; Wilson and Hart, 2001, supra). Therefore, our findings further emphasize the essential role of GP in providing protective immunity against filoviruses and indicate the requirement for the relevant GP in a pan-filovirus vaccine. In guinea pigs, mVLPs derived from MARV-Musoke, are able to broadly protect against MARV-Musoke, -Ravn, and -Ci67 infection (Table 2). We are also examining the protective efficacy of multivalent VLPs containing GP from multiple filovirus strains generated in particles containing a single VP40 molecule as another candidate for broad protection against all known strains of EBOV and MARV. The GP on the surface of the Ebola or Marburg virion is comprised of disulfide-linked GP1 and GP2 subunits, which are generated by proteolytic cleavage. For both EBOV and MARV, vaccination with either GP1 or GP2 expressed in a VRP backbone is sufficient for protection against homologous viral challenge (unpublished data). Further, monoclonal antibodies directed against either GP1 or GP2 confer protection from EBOV infection in mice (Wilson et al., 2000, Science 287, 1664-6). Ongoing studies are focused on the requirements for GP1 and GP2 in VLP-mediated protection by generating and examining the protective efficacy of heterologous fusions of GP1 and GP2 from EBOV and MARV on a single VP40 backbone. A single component VLP-based multivalent vaccine would be preferable for broad protection against lethal infection with multiple filovirus strains.

Vaccination with a mixture of eVLP and mVLP induced high levels of filovirus-specific serum antibodies, similar to those induced by vaccination with eVLP or mVLP alone. Therefore, concurrent vaccination with eVLP and mVLP did not quench the immune response to the individual viruses. While a single vaccination with eVLP or mVLP induced strong humoral responses to the homologous antigen, there were only negligible levels of antibodies that recognized the heterologous antigen (FIG. 18). Boosting with the homologous VLP results in a slight increase (10- to 30-fold) in antibody responses towards the heterotypic virus (Sullivan et al., 2003, supra). However, the heterotypic responses induced by eVLP or mVLP vaccination alone are not sufficient to protect against lethal infection with heterologous virus (Sullivan et al., 2003, supra). Administration of repeated doses of a mixture of eVLP and mVLP or alternating vaccinations with eVLP and mVLP may drive stronger heterotypic immune responses. A recent report showed that boosting papillomavirus-immune mice with chimeric papillomavirus VLPs can overcome inhibition of antigen presentation due to the presence of neutralizing antibodies (Wool-Lewis and Bates, 1998, J. Virol. 72, 3155-60). Administration of the chimeric VLPs augmented both cellular and humoral homotypic and heterotypic responses, which could lead to protection against broader papillomavirus infections (Wool-Lewis and Bates, 1998, supra). Therefore, altering the vaccine schedule or boosting with alternating VLP types or chimeric VLPs may broaden the heterotypic immune responses and increase protection against the multiple strains of EBOV and MARV.

We and others have noted that in both rodents and nonhuman primates, ineffectual vaccination can cause an accelerated filovirus disease progression and "early-death" phenomenon (Hevey et al., 1997, supra; Reimenschneider et al., 2003, supra; Sullivan, 2003, supra; Xu et al, 1998, supra). In fact, we have observed that vaccination with eVLP appeared to decrease the time to death following MARV challenge, when compared to control guinea pigs (Sullivan et al., 2003, supra). A similar, potentiated "early-death" phenomenon was observed in MARV-immune mice, challenged with EBOV, and inactivated MARV-vaccinated guinea pigs, challenged with MARV (Riemenschneider et al., 2003, supra; Xu et al., 1998, supra). Ineffectual MARV vaccination of monkeys can also result in a decreased time to death compared to unvaccinated monkeys following MARV challenge (Hevey et al., 1997, supra; Xu et al., 1998, supra; Yang et al., 2003, J. Virol. 77, 799-803). However, in this set of experiments, we did not observe accelerated disease symptoms or lethality in VLP-vaccinated guinea pigs challenged with heterologous virus (Table 1). This difference in our current work may be due to administration of only a single dose of vaccine, compared to the use of multiple vaccine doses in our previous work. We feel it is likely that the induction of poor homotypic or heterotypic immune responses augments filovirus pathogenesis. A single VLP vaccination seems to be sufficient to induce protective immunity against homologous challenge, but does not induce more severe disease upon challenge with a heterologous virus.

In summary, our data demonstrated the ability of a Marburg and Ebola VLP-based vaccine to induce strong antibody responses that correlated with protection from EBOV and MARV challenge. Vaccination with this multivalent VLP vaccine protected guinea pigs from viremia and death caused by a lethal challenge with EBOV or MARV. Using hybrid VLPs consisting of heterologous GP and VP40 molecules from EBOV and MARV, we show that GP is required and sufficient to protect against a lethal filovirus challenge. The correlates and mechanisms of protective immunity generated by GP and other filovirus proteins are not fully understood at this time; however, elucidation of these markers are critical for eventual FDA licensing of filovirus vaccines, as efficacy trials of EBOV and MARV vaccines are unlikely. In general, VLPs are unique when considering their advantages, including safety, ease of production and administration, lack of interference by an immunodominant vector backbone, concern of prior vector immunity, and the presentation of the relevant filovirus antigens in their native form.

All documents cited herein are hereby incorporated in their entirety by reference thereto.

What is claimed is:

1. A filovirus virus like particle (VLP) comprising filovirus envelope glycoprotein (GP) and filovirus matrix protein VP40.

2. A filovirus VLP, produced by expressing in a cell a polynucleotide encoding filovirus envelope glycoprotein and filovirus matrix protein VP40 such that said polynucleotide is expressed and said VLP is produced.

3. A VLP of claim 1 where said filovirus is chosen from the group consisting of Ebola and Marburg.

4. A VLP of claim 2 where said filovirus is chosen from the group consisting of Ebola and Marburg.

5. A filovirus vaccine comprising VLP according to claim 1.

6. A filovirus vaccine comprising VLP according to claim 2.

7. A filovirus vaccine according to claim 6 further comprising an adjuvant.

8. The vaccine of claim 7 wherein said adjuvant is chosen from the group consisting of: RIBI, QS21 and LT(R192G).

9. A filovirus vaccine according to claim 5 wherein said filovirus is chosen from the group consisting of Ebola and Marburg.

10. A filovirus vaccine according to claim 6 wherein said filovirus is chosen from the group consisting of Ebola and Marburg.

11. A filovirus vaccine comprising VLP according to claim 1 and a nucleic acid encoding an agent capable of eliciting an immune response against said filovirus.

12. An Ebola VLP-producing cell comprising a mammalian cell expressing Ebola GP and VP40.

13. A kit for the detection of Ebola virus infection comprising Ebola VLPs according to claim 3.

14. A kit for the detection of Marburg virus infection comprising Marburg VLPs according to claim 3.

15. A kit for testing agents involved in Ebola budding said kit comprising a cell producing Ebola VLPs according to claim 12 and ancillary reagents for detecting VLPs in the supernatant of said cells when cells are cultured.

16. A Marburg VLP-producing cell comprising a mammalian cell expressing Marburg GP and VP40.

17. A kit for testing agents involved in Marburg budding said kit comprising a cell producing Marburg VLPs according to claim 16 and ancillary reagents for detecting VLPs in the supernatant of said cells when cells are cultured.

18. An immunogenic composition comprising, in a physiologically acceptable vehicle, Ebola VLPs according to claim 4.

19. The immunogenic composition according to claim 18 which further comprises an adjuvant to enhance the immune response.

20. The immunogenic composition of claim 18, wherein said Ebola VLPs are produced by expressing in a mammalian cell Ebola GP and Ebola VP40.

21. An immunogenic composition comprising, in a physiologically acceptable vehicle, Marburg VLPs according to claim 4.

22. The immunogenic composition according to claim 21 which induces a Marburg specific immune response in a subject.

23. The immunogenic composition according to claim 21, which further comprises an adjuvant to enhance the immune response.

24. The immunogenic composition of claim 21, wherein said Marburg VLPs are produced by expressing in a mammalian cell Marburg GP and Marburg VP40.

25. A panfilovirus vaccine comprising a mixture of EBOV and MARV VLPs according to claim 4.

26. A MARV vaccine protective against infection with MARV-Musoke, MARV-Ravn, and MARV-Ci67, comprising MARV VLPs according to claim 4 consisting essentially of GP and VP40 from MARV-Musoke.

27. An Ebola VLP producing cell comprising an insect cell expressing Ebola GP and VP40.

28. A Marburg VLP producing cell comprising an insect cell expressing Marburg GP and VP40.

29. A filovirus virus like particle (VLP) comprising filovirus envelope glycoprotein (GP), filovirus matrix protein VP40, and filovirus nucleoprotein (NP).

30. A filovirus VLP, produced by expressing in a cell a polynucleotide encoding filovirus envelope glycoprotein, filovirus matrix protein VP40, and filovirus nucleoprotein NP, such that said polynucleotide is expressed and said VLP is produced.

31. The filovirus VLP according to claim 30 wherein said cell is chosen from the group consisting of mammalian cell and insect cell.

32. A VLP of claim 29 where said filovirus is chosen from the group consisting of Ebola and Marburg.

33. A VLP of claim 30 where said filovirus is chosen from the group consisting of Ebola and Marburg.

34. A filovirus vaccine comprising VLP according to claim 29.

35. A filovirus vaccine comprising VLP according to claim 30.

36. A filovirus vaccine according to claim 34 further comprising an adjuvant.

37. The vaccine of claim 36 wherein said adjuvant is chosen from the group consisting of: RIBI, QS21 and LT(R192G).

38. A filovirus vaccine according to claim 34 wherein said filovirus is chosen from the group consisting of Ebola and Marburg.

39. A filovirus vaccine according to claim 35 wherein said filovirus is chosen from the group consisting of Ebola and Marburg.

40. A filovirus vaccine comprising VLP according to claim 29 and a nucleic acid encoding an agent capable of eliciting an immune response against said filovirus.

41. An Ebola VLP-producing cell wherein said cell expresses Ebola GP, VP40, and NP.

42. A method for detecting Ebola virus infection comprising contacting a sample from a subject suspected of having Ebola virus infection with an Ebola VLP according to claim 32 and detecting the presence or absence of an infection by detecting the presence or absence of a complex formed between the Ebola VLP and antibodies specific therefor in said sample.

43. A kit for the detection of Ebola virus infection comprising Ebola VLPs according to claim 32.

44. A method for detecting Marburg virus infection comprising contacting a sample from a subject suspected of having Marburg virus infection with a Marburg VLP according to claim 32 and detecting the presence or absence of an infection by detecting the presence or absence of a complex formed between the Marburg VLP and antibodies specific therefor in said sample.

45. A kit for the detection of Marburg virus infection comprising Marburg VLPs according to claim 32.

46. A kit for testing agents involved in Ebola budding said kit comprising a cell producing Ebola VLPs according to claim 41 and ancillary reagents for detecting VLPs in the supernatant of said cells when cells are cultured.

47. A Marburg VLP-producing cell wherein said cell expresses Marburg GP, VP40, and NP.

48. A kit for testing agents involved in Marburg budding said kit comprising a cell producing Marburg VLPs according to claim 47 and ancillary reagents for detecting VLPs in the supernatant of said cells when cells are cultured.

49. An immunogenic composition comprising, in a physiologically acceptable vehicle, Ebola VLPs according to claim 32.

50. The immunogenic composition according to claim 49 which further comprises an adjuvant to enhance the immune response.

51. The immunogenic composition of claim 50, wherein said Ebola VLPs are produced by expressing in an insect cell Ebola GP, Ebola VP40, and Ebola NP.

52. An immunogenic composition comprising, in a physiologically acceptable vehicle, Marburg VLPs according to claim 32.

53. The immunogenic composition according to claim 52 which induces a Marburg specific immune response in a subject.

54. The immunogenic composition according to claim 52, which further comprises an adjuvant to enhance the immune response.

55. The immunogenic composition of claim 52, wherein said Marburg VLPs are produced by expressing in an insect cell Marburg GP, Marburg VP40, and Marburg NP.

56. A panfilovirus vaccine comprising a mixture of EBOV and MARV VLPs according to claim 32.

57. The immunogenic composition according to claim 18 which induces an Ebola specific immune response in a subject.

58. The filovirus VLP according to claim 31 wherein said filovirus is chosen from the group consisting of Ebola and Marburg.

* * * * *